United States Patent
Higgins et al.

(10) Patent No.: US 9,763,875 B2
(45) Date of Patent: Sep. 19, 2017

(54) IMPLANTABLE DEVICE FOR PRODUCTION OF INTERLEUKIN-1 RECEPTOR ANTAGONIST

(75) Inventors: Joel C. Higgins, Claypool, IN (US); James M. McKale, Cincinnati, OH (US); Jennifer E. Woodell-May, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

(21) Appl. No.: 13/392,266

(22) PCT Filed: Aug. 27, 2010

(86) PCT No.: PCT/US2010/046994
§ 371 (c)(1),
(2), (4) Date: Feb. 24, 2012

(87) PCT Pub. No.: WO2011/031553
PCT Pub. Date: Mar. 17, 2011

(65) Prior Publication Data
US 2012/0172836 A1   Jul. 5, 2012

Related U.S. Application Data

(60) Provisional application No. 61/237,484, filed on Aug. 27, 2009.

(51) Int. Cl.
*A61M 5/00*  (2006.01)
*A61K 9/00*  (2006.01)
(Continued)

(52) U.S. Cl.
CPC ............ *A61K 9/0024* (2013.01); *A61K 35/14* (2013.01); *A61K 35/15* (2013.01); *A61K 35/16* (2013.01);
(Continued)

(58) Field of Classification Search
None
See application file for complete search history.

(56) References Cited

U.S. PATENT DOCUMENTS 4,708,799 A   11/1987   Gerlach et al.
4,853,137 A    8/1989   Ersson
(Continued)

FOREIGN PATENT DOCUMENTS

AU       748575 B2     6/2002
CA      2772084 C     10/2016
(Continued)

OTHER PUBLICATIONS

Lavi, Galia; et al; "Sustained delivery of IL-1Ra from biodegradable microspheres reduces the number of murine B16 melanoma lung metastases" Journal of Controlled Release, 123, 123-130, 2007.*
(Continued)

*Primary Examiner* — David Berke-Schlessel
(74) *Attorney, Agent, or Firm* — Schwegman Lundberg & Woessner, P.A.

(57) ABSTRACT

Treatments and devices for generating and using interleukin-1 receptor antagonist (IL-1ra). An implantable device is loaded with adipose tissue and/or white blood cells and inserted into an inflammation site in a patient to produce interleukin-1 receptor antagonist in vivo. The implantable device has an enclosed or substantially enclosed body that defines an internal space. At least a portion of the body comprises a first bioresorbable material and a second bioresorbable material is within the internal space along with one or more voids. The second bioresorbable material includes an activation surface to activate adipose tissue and/or white blood cells loaded into the device to produce IL-1ra.

37 Claims, 3 Drawing Sheets

(51) Int. Cl.
*A61K 35/14* (2015.01)
*A61K 35/15* (2015.01)
*A61K 35/16* (2015.01)
*A61K 35/19* (2015.01)
*A61K 35/35* (2015.01)
*A61K 38/20* (2006.01)
*A61M 37/00* (2006.01)

(52) U.S. Cl.
CPC ............. *A61K 35/19* (2013.01); *A61K 35/35* (2013.01); *A61K 38/20* (2013.01); *A61M 37/0069* (2013.01)

(56) References Cited

U.S. PATENT DOCUMENTS

| | | |
|---|---|---|
| 5,075,222 A | 12/1991 | Hannum et al. |
| 5,359,032 A | 10/1994 | Dayer et al. |
| 5,571,418 A | 11/1996 | Lee et al. |
| 5,585,007 A | 12/1996 | Antanavich et al. |
| 5,599,558 A | 2/1997 | Gordinier et al. |
| 5,707,331 A | 1/1998 | Wells et al. |
| 5,788,662 A | 8/1998 | Antanavich et al. |
| 5,792,450 A | 8/1998 | Wilson et al. |
| 5,842,477 A | 12/1998 | Naughton et al. |
| 6,063,297 A | 5/2000 | Antanavich et al. |
| 6,096,728 A | 8/2000 | Collins et al. |
| 6,214,338 B1 | 4/2001 | Antanavich et al. |
| 6,287,558 B1* | 9/2001 | Lanza et al. ................ 424/93.7 |
| 6,337,072 B1 | 1/2002 | Ford et al. |
| 6,398,972 B1 | 6/2002 | Blasetti et al. |
| 6,599,873 B1 | 7/2003 | Sommer et al. |
| 6,623,472 B1 | 9/2003 | Reincke et al. |
| 6,649,072 B2 | 11/2003 | Brandt et al. |
| 6,713,246 B1 | 3/2004 | Reinecke et al. |
| 6,759,188 B2 | 7/2004 | Reinecke et al. |
| 6,790,371 B2 | 9/2004 | Dolocek |
| 6,811,777 B2 | 11/2004 | Mishra |
| 6,835,377 B2 | 12/2004 | Goldberg et al. |
| 6,905,612 B2 | 6/2005 | Dorian et al. |
| 7,011,852 B2 | 3/2006 | Sukavaneshvar et al. |
| 7,166,283 B2 | 1/2007 | Tsuji et al. |
| 7,179,391 B2 | 2/2007 | Leach et al. |
| 7,223,346 B2 | 5/2007 | Dorian et al. |
| 7,374,678 B2 | 5/2008 | Leach et al. |
| 7,465,293 B2 | 12/2008 | Reinecke et al. |
| 7,470,371 B2 | 12/2008 | Dorian et al. |
| 7,553,413 B2 | 6/2009 | Dorian et al. |
| 7,608,258 B2 | 10/2009 | Mishra |
| 7,678,385 B2 | 3/2010 | Reddi |
| 7,694,828 B2 | 4/2010 | Swift et al. |
| 7,708,152 B2 | 5/2010 | Dorian et al. |
| 7,806,276 B2 | 10/2010 | Leach et al. |
| 7,867,765 B2 | 1/2011 | Faustman et al. |
| 7,901,344 B2 | 3/2011 | Yoo |
| 7,901,584 B2 | 3/2011 | Dorian et al. |
| 7,914,689 B2 | 3/2011 | Higgins et al. |
| 7,992,725 B2 | 8/2011 | Leach et al. |
| 8,048,297 B2 | 11/2011 | Leach et al. |
| 8,048,321 B2 | 11/2011 | Leach et al. |
| 8,202,539 B2 | 6/2012 | Behnam et al. |
| 8,753,690 B2 | 6/2014 | Higgins et al. |
| 2001/0053764 A1 | 12/2001 | Sims et al. |
| 2002/0077276 A1 | 6/2002 | Fredeking et al. |
| 2002/0119179 A1 | 8/2002 | Rezania et al. |
| 2003/0055511 A1 | 3/2003 | Schryver et al. |
| 2003/0091536 A1 | 5/2003 | Frisbie et al. |
| 2003/0099650 A1 | 5/2003 | Ho et al. |
| 2003/0138910 A1 | 7/2003 | Reinecke et al. |
| 2003/0194397 A1 | 10/2003 | Mishra |
| 2003/0205538 A1 | 11/2003 | Dorian et al. |
| 2004/0120942 A1 | 6/2004 | McGinnis et al. |
| 2004/0182795 A1 | 9/2004 | Dorian et al. |
| 2004/0219182 A1 | 11/2004 | Gomes et al. |
| 2004/0251217 A1 | 12/2004 | Leach et al. |
| 2004/0258671 A1 | 12/2004 | Watkins |
| 2005/0084962 A1 | 4/2005 | Simon |
| 2005/0100536 A1 | 5/2005 | Mishra |
| 2005/0109716 A1 | 5/2005 | Leach et al. |
| 2005/0152905 A1 | 7/2005 | Omoigui |
| 2005/0186120 A1 | 8/2005 | Dorian et al. |
| 2005/0196874 A1 | 9/2005 | Dorian et al. |
| 2005/0197293 A1 | 9/2005 | Mellis et al. |
| 2006/0046960 A1 | 3/2006 | McKay et al. |
| 2006/0051865 A1 | 3/2006 | Higgins et al. |
| 2006/0057223 A1 | 3/2006 | DiMauro et al. |
| 2006/0057693 A1 | 3/2006 | Simon |
| 2006/0121002 A1 | 6/2006 | Rolland et al. |
| 2006/0171948 A1 | 8/2006 | Weinstein et al. |
| 2006/0175242 A1 | 8/2006 | Dorian et al. |
| 2006/0175244 A1 | 8/2006 | Dorian et al. |
| 2006/0175268 A1 | 8/2006 | Dorian et al. |
| 2006/0243676 A1 | 11/2006 | Swift et al. |
| 2006/0263408 A1* | 11/2006 | Rezania et al. ............... 424/426 |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0027082 A1 | 2/2007 | Hasty et al. |
| 2007/0075016 A1 | 4/2007 | Leach |
| 2007/0092494 A1 | 4/2007 | Higgins et al. |
| 2007/0207161 A1 | 9/2007 | Ralph |
| 2007/0208321 A1 | 9/2007 | Leach et al. |
| 2008/0011684 A1 | 1/2008 | Dorian et al. |
| 2008/0019964 A1 | 1/2008 | Olmarker et al. |
| 2008/0064626 A1 | 3/2008 | Zanella |
| 2008/0193424 A1 | 8/2008 | McKale et al. |
| 2008/0217263 A1 | 9/2008 | Higgins et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2009/0014391 A1 | 1/2009 | Leach et al. |
| 2009/0047242 A1 | 2/2009 | Reinecke et al. |
| 2009/0101599 A1 | 4/2009 | Dorian et al. |
| 2009/0112146 A1 | 4/2009 | Wratten et al. |
| 2009/0181019 A1 | 7/2009 | Solinger |
| 2009/0191217 A1 | 7/2009 | de Wildt et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2009/0263319 A1 | 10/2009 | Wohabrebbi et al. |
| 2009/0317439 A1 | 12/2009 | Turzi et al. |
| 2010/0008992 A1 | 1/2010 | Ichim |
| 2010/0015129 A1 | 1/2010 | Abramson et al. |
| 2010/0055087 A1 | 3/2010 | Higgins et al. |
| 2010/0125236 A1 | 5/2010 | Bare et al. |
| 2010/0140182 A1 | 6/2010 | Chapman et al. |
| 2010/0198130 A1 | 8/2010 | Swift et al. |
| 2010/0226909 A1 | 9/2010 | Hecker et al. |
| 2010/0256595 A1 | 10/2010 | Leach et al. |
| 2011/0052561 A1 | 3/2011 | Hoeppner |
| 2011/0059082 A1 | 3/2011 | Germer et al. |
| 2011/0059083 A1 | 3/2011 | Aigner et al. |
| 2011/0059084 A1 | 3/2011 | Osterroth et al. |
| 2011/0129441 A1 | 6/2011 | Lentz |
| 2011/0189172 A1 | 8/2011 | Solinger et al. |
| 2011/0192804 A1 | 8/2011 | Landrigan et al. |
| 2011/0268708 A1 | 11/2011 | Lin et al. |
| 2012/0027746 A1 | 2/2012 | Dorian et al. |
| 2012/0093936 A1 | 4/2012 | Lindenberg et al. |
| 2012/0150086 A1 | 6/2012 | Cohen |
| 2012/0172836 A1 | 7/2012 | Higgins et al. |
| 2013/0178425 A1 | 7/2013 | Higgins et al. |
| 2013/0259951 A1 | 10/2013 | O'Connell, Jr. |

FOREIGN PATENT DOCUMENTS

| | | |
|---|---|---|
| EP | 0417818 A1 | 3/1991 |
| EP | 2186877 | 5/2010 |
| EP | 2470163 B1 | 9/2016 |
| WO | WO-9824477 A1 | 6/1998 |

(56) References Cited

FOREIGN PATENT DOCUMENTS

| WO | WO-99/05989 A2 | 2/1999 |
|---|---|---|
| WO | WO 99/67277 | 12/1999 |
| WO | 03063799 A2 | 8/2003 |
| WO | 03080104 A2 | 10/2003 |
| WO | 03088905 A2 | 10/2003 |
| WO | WO 2004/009207 | 1/2004 |
| WO | 2006/043972 A1 | 4/2006 |
| WO | WO 2007/121538 | 11/2007 |
| WO | WO-2007/128973 A2 | 11/2007 |
| WO | 2008/021237 A1 | 2/2008 |
| WO | WO 2011/031553 | 3/2011 |
| WO | WO-2011031553 A3 | 3/2011 |
| WO | WO 2012/030593 | 3/2012 |

OTHER PUBLICATIONS

Re, Fabio; et al; "Expression of interleukin-1 receptor antagonist (IL-ra) by human circulating polymorphonuclear cells" European Journal of Immunology, 23, 570-573, 1993.*

Arend, W. et al. "Interleukin-1 Receptor Antagonist: Role in Biology" Annu. Rev. Immunol., vol. 16 (pp. 27-55) 1998.

Bendele, A. et al. "Combination Benefit of Treatment with the Cytokine Inhibitors Interleukin-1 Receptor Antagonist and PEGylated Soluble Tumor Necrosis Factor Receptor Type 1 in Animal Models of Rheumatoid Arthritis" Arthritis & Rheumatism, vol. 43, No. 12 (pp. 2648-2659) Dec. 2000.

Biomet Biologics, Inc. "GPS® II Platelet Concentrate System: The New Gold Standard" Product Brochure (14 pages) Sep. 2006.

Biomet Biologics, Inc. "GPS® III Platelet Separation System" Product Brochure (8 pages) 2007.

Biomet Biologics, Inc. "Plasmax Plasma Concentrate" Product Brochure (6 pages) 2006.

Biomet Biologics, Inc. "Vortech Concentration System Product" Product Brochure (16 pages) Aug. 2005.

Biomet Biologics, Inc. "GPS System Shoulder Recovery with the GPS Platelet Concentrate System" Product Brochure (6 pages) 2004.

Bio-Rad Laboratories. Bio-Gel P Polyacrylamide Gel Instruction Manual, Obtained from www.bio-rad.com/webmaster/pdfs/9154_Bio-Gel_P.pdf on Jun. 20, 2012 (14 pages).

Burnouf, T. et al. "Blood-Derived, Tissue Engineering Biomaterials" Biomedical Engineering-Applications, Basis and Communications, vol. 16, No. 6 (pp. 294-304) Dec. 2004.

Cell Factor Technologies, Inc. "GPS® Platelet Concentrate System" Product Brochure (9 pages) 2004.

Cell Factor Technologies, Inc., Biomet Europe. "GPS® II System, Gravitational Platelet Separation System, Accelerating the Body's Natural Healing Process" Product Bruchure (16 pages) 2005, http://www.cellfactortech.com/global_products.cfm, printed Sep. 16, 2005.

Cell Factor Technologies, Inc., Biomet Europe. "GPS® II System, Gravitational Platelet Separation System" User Manual (13 pages), http://www.cellfactortech.com/global_products.cfm, printed Sep. 16, 2005.

Dallari et al. "Enhanced Tibial Osteotomy Healing with Use of Bone Grafts Supplemented with Platelet Gel or Platelet Gel and Bone Marrow Stromal Cells" The Journal of Bone and Joint Surgery, vol. 89 (2007) pp. 2413-2420.

Dinarello, C. "Interleukin-1 and Interleukin-1 Antagonism" Blood, vol. 77, No. 8 (pp. 1627-1652) Apr. 1991.

Eppley, et al. "Platelet Quantification and Growth Factor Analysis from Platelet-Rich Plasma: Implications for Wound Healing," Plastic and Reconstructive Surgery, 114(6):1502-1508 (Nov. 2004).

Juge-Aubry, C. et al. "Regulatory Effects of Interleukin (IL)-1, Interferon-β, and IL-4 on the Production of IL-1 Receptor Antagonist by Human Adipose Tissue" The Journal of Clinical Endocrinology & Metabolism, vol. 89, No. 6 (pp. 2652-2658) Jun. 2004.

Kaufman, A. et al. "Human macrophage response to UHMWPE, TiAlV, CoCr, and alumina particles: Analysis of multiple cytokines using protein arrays" Journal of Biomedical Materials Research Part A, published online in Wiley InterScience DOI: 10.1002/jbm.a.31467 (pp. 464-474) Jul. 2007.

Kim, S.H. et al. "Ex Vivo Gene Delivery of IL-1Ra and Soluble TNF Receptor Confers a Distal Synergistic Therapeutic Effect in Antigen-Induced Arthritis" Molecular Therapy, vol. 6, No. 5 (pp. 561-600) Nov. 2002.

Lucarelli, E. et al. "Platelet-derived growth factors enhance proliferation of human stromal stem cells" Biomaterials, vol. 24 (2003) pp. 3095-3100.

Matthews, J. et al. "Comparison of the response of primary human peripheral blood mononuclear phagocytes from different donors to challenge with model polyethylene particles of known size and dose" Biomaterials, vol. 21 (pp. 2033-2044) 2000.

Meier, H. et al. "The production of antiinflammatory cytokines in whole blood by physico-chemical induction" Inflamm. Res., vol. 52 (pp. 404-407) Oct. 2003.

Morizaki et al. "The Effects of Platelet-Rich Plasma on Bone Marrow Stromal Cell Transplants for Tendon Healing in Vitro" J. Hand Surg. Am., vol. 35, No. 11 (Nov. 2010) pp. 1833-1841.

Muzio, M. et al. "Interleukin-13 Induces the Production of Interleukin-1 Receptor Antagonist (IL-1ra) and the Expression of the mRNA for the Intracellular (Keratinocyte) Form of IL-1ra in Human Myelomonocytic Cells" Blood, vol. 83, No. 7 (pp. 1738-1743) Apr. 1994.

Rader, C. et al. "Cytokine Response of Human Macrophage-like Cells After Contact With Polyethylene and Pure Titanium Particles" The Journal of Arthroplasty, vol. 14, No. 7 (pp. 840-848 (Oct. 1999).

Swift, M. et al. "Characterization of Growth Factors in Platelet Rich Plasma" Cell Factor Technologies, Inc. Printed Sep. 16, 2005 from www.cellfactortech.com/global_products.cfm.

Vangsness, T. et al. "Stimulation of IL-1ra Production from Platelet-Rich Plasma" Poster No. 488 presented at 54th Annual Meeting of the Orthopeadic Research Society in San Francisco, CA (1 page) Mar. 2-5, 2008.

Woodell-May, J. et al. "Effect of Incubation Time on Production of IL-1ra and sTNF-RI from Platelet-Rich Plasma" Paper No. 200, 55th Annual Meeting of the Orthopaedic Research Society (1 page) Feb. 2009.

Woodell-May, J. et al. "Elution of IL-1ra from a concentrated-plasma matrix—An in vitro study" Poster Presentation at 8th World Congress of the International Cartilage Repair Society, Miami, FL. (1 page) May 2009.

Woodell-May, J. et al. "Producing Accurate Platelet Counts for Platelet Rich Plasma: Validation of a Hematology Analyzer and Preparation Techniques for Counting" Scientific Foundation, Journal of Carniofacial Surgery, vol. 16, No. 5 (pp. 749-756) Sep. 2005.

Wright-Carpenter, T. "Treatment of Muscle Injuries by Local Administration of Autologous Conditioned Serum: A Pilot Study on Sportsmen with Muscle Strains" Int J Sports Med, vol. 25 (pp. 588-593) Oct. 2004.

Yang, S. et al. "Protective effects of IL-1Ra or vIL-10 gene transfer on a murine model of wear debris-induced osteolysis" Gene Therapy, vol. 11 (pp. 483-491) 2004.

Yang, T. et al. "Recent Applications of Polyacrylamide as Biomaterials" Recent Patents on Materials Science, vol. 1 (pp. 29-40) 2008.

C. E. Juge-Aubry et al: "Adipose Tissue Is a Major Source of Interleukin-1 Receptor Antagonist: Upregulation in Obesity and Inflammation", Diabetes, vol. 52, No. 5, May 1, 2003 (May 1, 2003), pp. 1104-1110, XP55001835, ISSN: 0012-1797, DOI: . 10.2337/diabetes.52.5.1104 p. 1107, left-hand column, paragraph 2-right-hand column, paragraph 1.

U.S. Appl. No. 12/394,723, filed Feb. 27, 2009, Higgins et al.
U.S. Appl. No. 12/549,015, filed Aug. 27, 2009, Higgins et al.
U.S. Appl. No. 12/549,116, filed Aug. 27, 2009, Hoeppner.

Alford, J. et al. "Cartilage Restoration, Part 1" The American Journal of Sports Medicine, vol. 33, No. 2 (2005) p. 295-306.

Anitua, E. et al. "Autologous platelets as a source of proteins for healing and tissue regeneration" Thromb Haemost, vol. 91 (pp. 4-15) 2004.

(56) References Cited

OTHER PUBLICATIONS

Anonymous: "Update for veterinarians" Dec. 2012. vet.osu.edu/sites/default/files/documents/pdf/news/vmc/ovmaVeternarianUp/date/20121112.pdf.
Baltzer AW, et al. Autologous conditioned serum (Orthokine) is an effective treatment for knee osteoarthritis. Osteoarthritis Cartilage Feb. 1, 2009; 17(2):152-60.
Becker C. et al. Efficacy of epidural perineural injections with autologous conditioned serum for lumbar radicular compression: an Investigator-initiated, prospective, double-blind, reference-controlled study. Spine Aug. 1, 2007; 32 (17):1803-8.
Bielecki, T. et al, "Antibacterial effect of autologous platelet gel enriched with growth factors and toher acive substances" J Bone Joint Surg, vol. 89-B, No. 3 (p. 417-420) Mar. 2007.
Dinarello, C. A. Interleukin-1 in the pathogenesis and treatment of inflammatory diseases. Blood, 2011, vol. 117 (14), p. 3720-3732.
Evans, C.H.Novel biological approaches to the intra-articular treatment of osteoarthritis. BioDrugs 2005; 19(6):355-62.
Fiotti et al. "Atherosclerosis and Inflammation. Patterns of Cytokine Regulation in Patients with Peripheral Arterial Disease" Atherosclerosis, Elsevier Ireland Ltd, IE, vol. 145, No. 1, pp. 51-60. Jul. 1, 1999.
Floryan, K. et al. "Home Study Program: Intraoperative use of Autologous Platelet-Rich and Platelet-Poor Plasma for Orthopedic Surgery Patients" vol. 80, No. 4 (Oct. 2004) p. 667-674.
Hou, WH et al. "Microfluidic Devices for Blood Fractionation" Micromachines (2011) 2, 319-343.
Juge-Aubry, C. et al. "Adipose Tissue is a Major Source of Interleukin-1 Receptor Antagonist" Diabetes, vol. 52, May 2003 (pp. 1104-1110).
Kim, Seon Hee et al. "Ex vivo gene delivery of Il-1Ra and soluble TNF receptor confers a distal synergistic therapeutic effect in antigen-induced arthritis", Molecular Therapy, vol. 6, No. 5, Nov. 1, 2002 (pp. 591-600).
King, W. et al. "A simple method to Correlate the Concentration of an Anti-Inflammatory Cytokine with White Blood Cells in an Autologous Protein Solution" Feb. 24, 2014.
Klingenberg et al. "Treating inflammation in Atherosclerotic Cardiovascular Disease: Emerging Therapies" European Heart Journal., vol. 30, No. 23, pp. 2838-2844, Dec. 2009.
Meijer, H. et al. "The production of antiinflammatory cytokines in whole blood by physico-chemical induction" Inflamm. Res., vol. 52 (pp. 404-407) Oct. 2003.
Miltenyi Biotec GmbH, Isolation of Granulocytes From Human Peripheral Blood by Density Gradient Centrifugation (2008) 2 pages.
Murphy et al. "Autologous Bone Marrow Mononuclear Cell Therapy is Safe and Promotes Amputation-free Survival in Patients with Critical Limb Ischemia" Journal of Vascular Surgery, C.V. Mosby Co., vol. 53, No. 6, Jan. 28, 2011.
Nursen Düzgün et al. "Cytokine inhibitors: soluble tumor necrosis factor receptor 1 and interleukin-1 receptor antagonist in Behçet's disease" Rheumatology International ; Clinical and Experimental Investigations, Springer, Berlin, DE vol. 25, No. 1, Jan. 2005. p. 1-5.
O'Shaughnessey, K.M. et al. Blood-derived anti-inflammatory protein solution blocks the effect of IL-1beta on human macrophages in vitro. Inflamm Res Oct. 2011; 60(10):929-36.
Plasmax® Plasma Concentration System. 2007. Biomet Biologics. p. 1-20.
Rader, C. et al. "Cytokine Response of Human Macrophage-like Cells After Contact With Polyethylene and Pure Titanium Particles" The Journal of Arthroplasty, vol. 14, No. 7 pp. 840-848 (Oct. 1999).
Sorbera L A "Pegsunercept. Pegylated Soluble Tumor Necrosis Factor Receptor Type 1 PEG-STNF-RI" Drugs of the Future, Prous Science, ES, vol. 28, No. 12. Jan. 1, 2003. p. 1182-1188.
Tateishi-Yuyama, E. et al. "Therapeutic angiogenesis for patients with limb ischaemia by autologous transplantation of bone-barrow cells: a pilot study and randomised controlled trial" The Lancet 2002; 360:427-435.
Ulich, T.R. et al. "Intratrachael Administration of Endotoxin and Cytokines: IV. The Soluble Tumor Necrosis Factor Receptor Type 1 Inhibits Acute Inflammation" American Journal of Pathology; vol. 142, No. 5, May 1993.
Woodell-May, J. et al. Autologous protein solution inhibits MMP-13 production by IL-1beta and TNFalpha-stimulated human articular chondrocytes. J Orthop Res Sep. 15, 2011; 29:1320-6.
Yoshida S. et al. "Elevation of serum soluble tumour necrosis factor (TNF) receptor and IL-1 receptor antagonist levels in bronchial asthma" Clinical and Experimental Immunology, Wiley-Blackwell Publishing Ltd. vol. 106, No. 1, Oct. 1996.
Zhang et al."IL-1ra alleviates inflammatory hyperalgesia through preventing phosphorylation of NMDA receptor NR-1 subunit in rats" Pain. vol. 135, No. 3, Mar. 5, 2008, pp. 232-239.
"Canadian Application Serial No. 2,772,084, Office Action mailed Jun. 11, 2015", 3 pgs.
"European Application Serial No. 10749582.2, Examination Notification Art. 94(3) mailed Dec. 8, 2014", 7 pgs.
"Japanese Application Serial No. 2012-527030, Office Action mailed Jun. 12, 2015", (English Translation), 2 pgs.
"A phase I safety study of combination treatment with pegylated soluble tumor necrosis factor receptor type I (PET STNF-RI) and anakinra (interleukin-1 receptor antagonist, IL-1RA) in patients with rheumatoid arthritis", Prous integrity, (Jun. 12, 2002), 1-1.
"U.S. Appl. No. 12/101,586, Final Office Action mailed Feb. 3, 2011", 11 pgs.
"U.S. Appl. No. 12/101,586, Non Final Office Action mailed Sep. 20, 2010", 12 pgs.
"U.S. Appl. No. 12/101,586, Notice of Allowance mailed Mar. 24, 2011", 5 pgs.
"U.S. Appl. No. 12/101,594, Final Office Action mailed Mar. 18, 2010", 8 pgs.
"U.S. Appl. No. 12/101,594, Non Final Office Action mailed Oct. 16, 2009", 8 pgs.
"U.S. Appl. No. 12/101,594, Notice of Allowance mailed May 27, 2010", 7 pgs.
"U.S. Appl. No. 12/394,723, Advisory Action mailed Dec. 19, 2014", 3 pgs.
"U.S. Appl. No. 12/394,723, Appeal Brief filed Jun. 15, 2015", 42 pgs.
"U.S. Appl. No. 12/394,723, Decision on Pre-Appeal Brief mailed Feb. 13, 2015", 2 pgs.
"U.S. Appl. No. 12/394,723, Examiner's Answer to Appeal Brief mailed Sep. 9, 2015", 11 pgs.
"U.S. Appl. No. 12/394,723, Final Office Action mailed Apr. 19, 2016", 13 pgs.
"U.S. Appl. No. 12/394,723, Final Office Action mailed Jun. 26, 2012", 11 pgs.
"U.S. Appl. No. 12/394,723, Final Office Action mailed Sep. 8, 2014", 8 pgs.
"U.S. Appl. No. 12/394,723, Non Final Office Action mailed Feb. 7, 2014", 8 pgs.
"U.S. Appl. No. 12/394,723, Non Final Office Action mailed Oct. 31, 2011", 11 pgs.
"U.S. Appl. No. 12/394,723, Non Final Office Action mailed Dec. 24, 2015", 9 Pgs.
"U.S. Appl. No. 12/394,723, Response filed Jan. 8, 2015 to Pre-Appeal Brief Request mailed Dec. 19, 2014", 4 pgs.
"U.S. Appl. No. 12/394,723, Response filed Apr. 30, 2012 to Non Final Office Action mailed Oct. 31, 2011", 16 pgs.
"U.S. Appl. No. 12/394,723, Response filed Jul. 23, 2014 to Non Final Office Action mailed Feb. 7, 2014", 19 pgs.
"U.S. Appl. No. 12/394,723, Response filed Aug. 19, 2016 to Final Office Action mailed Apr. 19, 2016", 23 pgs.
"U.S. Appl. No. 12/394,723, Response filed Aug. 22, 2011 to Restriction Requirement mailed Jul. 20, 2011", 2 pgs.
"U.S. Appl. No. 12/394,723, Response filed Nov. 9, 2015 to Final Office Action mailed Sep. 8, 2014", 19 pgs.
"U.S. Appl. No. 12/394,723, Response filed Dec. 10, 2014 to Final Office Action mailed Sep. 8, 2014", 18 pgs.
"U.S. Appl. No. 12/394,723, Response filed Dec. 19, 2012 to Final Office Action mailed Jun. 26, 2012", 16 pgs.

(56) References Cited

OTHER PUBLICATIONS

"U.S. Appl. No. 12/394,723, Restriction Requirement mailed Jul. 20, 2011", 7 pgs.
"U.S. Appl. No. 12/394,723, Response filed Mar. 24, 2016 to Non Final Office Action mailed Dec. 24 ,2015", 18 pgs.
"U.S. Appl. No. 12/549,015, Examiner Interview Summary mailed Dec. 3, 2012", 3 pgs.
"U.S. Appl. No. 12/549,015, Final Office Action mailed Aug. 16, 2012", 8 pgs.
"U.S. Appl. No. 12/549,015, Non Final Office Action mailed Mar. 9, 2012", 8 pgs.
"U.S. Appl. No. 12/549,015, Notice of Allowance mailed Feb. 3, 2014", 9 pgs.
"U.S. Appl. No. 12/549,015, Response filed Feb. 9, 2012 to Restriction Requirement mailed Jan. 9, 2012", 2 pgs.
"U.S. Appl. No. 12/549,015, Response filed Jul. 6, 2012 to Non Final Office Action mailed Mar. 9, 2012", 12 pgs.
"U.S. Appl. No. 12/549,015, Response filed Dec. 17, 2012 to Final Office Action mailed Aug. 16, 2012", 17 pgs.
"U.S. Appl. No. 12/549,015, Restriction Requirement mailed Jan. 9, 2012", 5 pgs.
"U.S. Appl. No. 12/549,116, Decision on Pre-Appeal Brief mailed Feb. 5, 2015", 2 pgs.
"U.S. Appl. No. 12/549,116, Examiner Interview Summary mailed Dec. 5, 2012", 3 pgs.
"U.S. Appl. No. 12/549,116, Final Office Action mailed Jan. 4, 2016", 15 pgs.
"U.S. Appl. No. 12/549,116, Final Office Action mailed Aug. 8, 2012", 20 pgs.
"U.S. Appl. No. 12/549,116, Final Office Action mailed Oct. 8, 2014", 12 pgs.
"U.S. Appl. No. 12/549,116, Non Final Office Action mailed Feb. 24, 2012", 16 pgs.
"U.S. Appl. No. 12/549,116, Non Final Office Action mailed Jun. 4, 2015", 12 pgs.
"U.S. Appl. No. 12/549,116, Non Final Office Action mailed Jun. 5, 2014", 15 pgs.
"U.S. Appl. No. 12/549,116, Pre-Appeal Brief Request filed Jan. 8, 2015", 5 pgs.
"U.S. Appl. No. 12/549,116, Response filed Jan. 8, 2013 to Final Office Action mailed Aug. 8, 2012", 14 pgs.
"U.S. Appl. No. 12/549,116, Response filed Jan. 13, 2012 to Restriction Requirement mailed Dec. 13, 2011", 3 pgs.
"U.S. Appl. No. 12/549,116, Response filed Mar. 3, 2016 to Final Office Action mailed Jan. 4, 2016", 11 pgs.
"U.S. Appl. No. 12/549,116, Response filed Jun. 25, 2012 to Non Final Office Action mailed Feb. 24, 2012", 14 pgs.
"U.S. Appl. No. 12/549,116, Response filed Sep. 4, 2015 to Non Final Office Action mailed Jun. 4, 2015", 9 pgs.
"U.S. Appl. No. 12/549,116, Response filed Sep. 5, 2014 to Non Final Office Action mailed Jun. 5, 2014", 11 pgs.
"U.S. Appl. No. 12/549,116, Restriction Requirement mailed Dec. 13, 2011", 6 pgs.
"U.S. Appl. No. 12/897,401, Non Final Office Action mailed Nov. 16, 2010", 9 pgs.
"U.S. Appl. No. 12/897,401, Notice of Allowance mailed Oct. 18, 2011", 6 pgs.
"U.S. Appl. No. 13/782,421, Final Office Action mailed Jan. 15, 2015", 30 pgs.
"U.S. Appl. No. 13/782,421, Non Final Office Action mailed Jul. 3, 2014", 26 pgs.
"U.S. Appl. No. 13/782,421, Non Final Office Action mailed Sep. 30, 2013", 30 pgs.
"U.S. Appl. No. 13/782,421, Notice of Allowance mailed Apr. 27, 2015", 8 pgs.
"U.S. Appl. No. 13/782,421, Preliminary Amendment filed Mar. 1, 2013", 8 pgs.
"U.S. Appl. No. 13/782,421, Response filed Feb. 26, 2014 to Non Final Office Action mailed Sep. 30, 2013", 21 pgs.
"U.S. Appl. No. 13/782,421, Response filed Apr. 15, 2015 to Final Office Action mailed Jan. 15, 2015", 6 pgs.
"U.S. Appl. No. 13/782,421, Response filed Jul. 3, 2013 to Restriction Requirement mailed Jun. 4, 2013", 2 pgs.
"U.S. Appl. No. 13/782,421, Response filed Oct. 3, 2014 to Non Final Office Action mailed Jul. 3, 2014", 15 pgs.
"U.S. Appl. No. 13/782,421, Restriction Requirement mailed Jun. 4, 2013", 6 pgs.
"U.S. Appl. No. 13/837,005, Final Office Action mailed Aug. 23, 2016", 9 pgs.
"U.S. Appl. No. 13/837,005, Final Office Action mailed Dec. 5, 2014", 9 pgs.
"U.S. Appl. No. 13/837,005, Non Final Office Action mailed Feb. 17, 2016", 13 pgs.
"U.S. Appl. No. 13/837,005, Non Final Office Action mailed May 13, 2014", 10 pgs.
"U.S. Appl. No. 13/837,005, Non Final Office Action mailed Jun. 9, 2015", 13 pgs.
"U.S. Appl. No. 13/837,005, Response filed Jan. 3, 2014 to Restriction Requirement mailed Dec. 3, 2013", 4 pgs.
"U.S. Appl. No. 13/837,005, Response filed Mar. 5, 2015 to Final Office Action mailed Dec. 5, 2014", 11 pgs.
"U.S. Appl. No. 13/837,005, Response filed May 17, 2016 to Non Final Office Action mailed Feb. 17, 2016", 13 pgs.
"U.S. Appl. No. 13/837,005, Response filed Aug. 13, 2014 to Non Final Office Action mailed May 13, 2014", 13 pgs.
"U.S. Appl. No. 13/837,005, Response filed Nov. 9, 2015 to Non Final Office Action mailed Jun. 9, 2015", 11 pgs.
"U.S. Appl. No. 13/837,005, Restriction Requirement mailed Dec. 3, 2013", 9 pgs.
"U.S. Appl. No. 13/837,480, Final Office Action mailed May 23, 2016", 11 pgs.
"U.S. Appl. No. 13/837,480, Non Final Office Action mailed Aug. 11, 2015", 10 pgs.
"U.S. Appl. No. 13/837,480, Response filed Jan. 11, 2016 to Non Final Office Action mailed Aug. 11, 2015", 14 pgs.
"U.S. Appl. No. 13/837,480, Response filed Nov. 5, 2014 to Restriction Requirement mailed Sep. 16, 2014", 3 pgs.
"U.S. Appl. No. 13/837,480, Restriction Requirement mailed Sep. 16, 2014", 6 pgs.
"U.S. Appl. No. 13/839,280, Final Office Action mailed Apr. 10, 2015", 17 pgs.
"U.S. Appl. No. 13/839,280, Non Final Office Action mailed Apr. 7, 2016", 16 pgs.
"U.S. Appl. No. 13/839,280, Non Final Office Action mailed Jul. 17, 2014", 12 pgs.
"U.S. Appl. No. 13/839,280, Response filed Mar. 17, 2014 to Restriction Requirement mailed Jan. 15, 2014", 5 pgs.
"U.S. Appl. No. 13/839,280, Response filed Aug. 29, 2016 to Non Final Office Action mailed Apr. 7, 2016", 15 pgs.
"U.S. Appl. No. 13/839,280, Response filed Oct. 12, 2015 to Final Office Action mailed Apr. 10, 2015", 9 pgs.
"U.S. Appl. No. 13/839,280, Response filed Oct. 17, 2014 to Non Final Office Action mailed Jul. 17, 2014", 19 pgs.
"U.S. Appl. No. 13/839,280, Restriction Requirement mailed Jan. 15, 2014", 6 pgs.
"U.S. Appl. No. 13/840,129, Final Office Action mailed Jun. 18, 2015", 9 pgs.
"U.S. Appl. No. 13/840,129, Non Final Office Action mailed Oct. 23, 2014", 8 pgs.
"U.S. Appl. No. 13/840,129, Response filed Feb. 23, 2015 to Non Final Office Action mailed Oct. 23, 2014", 15 pgs.
"U.S. Appl. No. 13/840,129, Restriction Requirement mailed Mar. 14, 2014", 6 pgs.
"U.S. Appl. No. 13/840,562, Final Office Action mailed Jan. 20, 2016", 14 pgs.
"U.S. Appl. No. 13/840,562, Non Final Office Action mailed Apr. 24, 2015", 23 pgs.
"U.S. Appl. No. 13/840,562, Non Final Office Action mailed Sep. 30, 2014", 19 pgs.
"U.S. Appl. No. 13/840,562, Response filed Mar. 21, 2014 to Restriction Requirement mailed Jan. 23, 2014", 9 pgs.

(56) References Cited

OTHER PUBLICATIONS

"U.S. Appl. No. 13/840,562, Response filed Apr. 18, 2016 to Final Office Action mailed Jan. 20, 2016", 18 pgs.
"U.S. Appl. No. 13/840,562, Response filed Jul. 29, 2015 to Non Final Office Action mailed Apr. 24, 2015", 13 pgs.
"U.S. Appl. No. 13/840,562, Response filed Dec. 30, 2014 to Non Final Office Action mailed Sep. 30, 2014", 17 pgs.
"U.S. Appl. No. 13/840,562, Restriction Requirement mailed Jan. 23, 2014", 9 pgs.
"U.S. Appl. No. 13/841,083, Examiner Summary", 1 pg.
"U.S. Appl. No. 13/841,083, Non Final Office Action mailed Jan. 29, 2016", 11 pgs.
"U.S. Appl. No. 13/841,083, Non Final Office Action mailed Jul. 15, 2015", 8 pgs.
"U.S. Appl. No. 13/841,083, Non Final Office Action mailed Dec. 10, 2014", 12 pgs.
"U.S. Appl. No. 13/841,083, Response filed Apr. 10, 2015 to Non Final Office Action mailed Dec. 10, 2014", 17 pgs.
"U.S. Appl. No. 13/841,083, Response filed Apr. 28, 2016 to Non Final Office Action mailed Jan. 29, 2016", 11 pgs.
"U.S. Appl. No. 13/841,083, Response filed Aug. 27, 2014 to Restriction Requirement mailed Jul. 21, 2014", 3 pgs.
"U.S. Appl. No. 13/841,083, Response filed Oct. 13, 2015 to Non Final Office Action mailed Jul. 15, 2015", 10 pgs.
"U.S. Appl. No. 13/841,080, Restriction Requirement mailed Jul. 21, 2014", 6 pgs.
"U.S. Appl. No. 13/841,103, Final Office Action mailed Aug. 13, 2015", 13 pgs.
"U.S. Appl. No. 13/841,103, Non Final Office Action mailed Jun. 7, 2016", 16 pgs.
"U.S. Appl. No. 13/841,103, Non Final Office Action mailed Dec. 4, 2014", 10 pgs.
"U.S. Appl. No. 13/841,103, Response filed Jan. 13, 2016 to Final Office Action mailed Aug. 13, 2015", 11 pg.
"U.S. Appl. No. 13/841,103, Response filed Apr. 18, 2016 to Restriction Requirement mailed Feb. 19, 2016", 8 pgs.
"U.S. Appl. No. 13/841,103, Response filed May 4, 2015 to Non Final Office Action mailed Dec. 4, 2014", 18 pgs.
"U.S. Appl. No. 13/841,103, Response filed Aug. 27, 2014 to Restriction Requirement mailed Jul. 21, 2014", 3 pgs.
"U.S. Appl. No. 13/841,103, Response filed Aug. 31, 2016 to Non Final Office Action mailed Jun. 7, 2016", 15 pgs.
"U.S. Appl. No. 13/841,103, Restriction Requirement mailed Feb. 19, 2016", 7 pgs.
"U.S. Appl. No. 13/841,103, Restriction Requirement mailed Jul. 21, 2014", 6 pgs.
"U.S. Appl. No. 13/987,480, Response filed Jul. 25, 2016 to Final Office Action mailed May 23, 2016", 13 pgs.
"U.S. Appl. No. 14/050,950, Final Office Action mailed Jun. 17, 2016", 9 pgs.
"U.S. Appl. No. 14/050,950, Non Final Office Action mailed Nov. 19, 2015", 13 pgs.
"U.S. Appl. No. 14/050,950, Response filed Feb. 19, 2016 to Non Final Office Action mailed Nov. 19, 2015", 11 pgs.
"U.S. Appl. No. 14/050,950, Response filed Jun. 23, 2015 to Restriction Requirement mailed Apr. 23, 2015", 1 pgs.
"U.S. Appl. No. 14/050,950, Response filed Aug. 17, 2016 to Final Office Action mailed Jun. 17, 2016", 8 pgs.
"U.S. Appl. No. 14/050,950, Restriction Requirement mailed Apr. 23, 2015", 7 pgs.
"U.S. Appl. No. 14/271,722, Notice of Allowance mailed Jan. 25, 2016", 13 pgs.
"U.S. Appl. No. 14/271,722, Preliminary Amendment filed May 7, 2014", 9 pgs.
"U.S. Appl. No. 14/803,414, Preliminary Amendment filed Sep. 16, 2015", 7 pgs.
"U.S. Appl. No. 14/803,414, Supplemental Preliminary Amendment Filed Feb. 3, 2016", 8 pgs.
"U.S. Appl. No. 14/808,828, Preliminary Amendment filed Jul. 24, 2015", 12 pgs.

"U.S. Appl. No. 14/808,828, Restriction Requirement mailed Aug. 2, 2016", 6 pgs.
"U.S. Appl. No. 14/808,828, Supplemental Preliminary Amendment filed Jul. 27, 2015", 10 pgs.
"U.S. Appl. No. 14/808,828, Supplemental Preliminary Amendment filed Oct. 6, 2015", 7 pgs.
"U.S. Appl. No. 14/830,977, Non Final Office Action mailed Apr. 13, 2016", 16 pgs.
"U.S. Appl. No. 14/830,977, Response filed Jul. 13, 2016 to Non Final Office Action mailed Apr. 13, 2016", 10 pgs.
"U.S. Appl. No. 14/973,913, Preliminary Amendment filed Mar. 2, 2016", 10 pgs.
"U.S. Appl. No. 13/840,129, Response filed May 14, 2014 to Restriction Requirement mailed Mar. 14, 2014", 3 pgs.
"Arthritis", [Online]. Retrieved from the Internet: Wayback Machine <URL:http://www.mayoclinic.org/diseases-conditions/arthritis/basics/treatment/con-20034095 >, (2014), 5 pgs.
"Australian Application Serial No. 2010292553, First Examiner Report mailed Feb. 7, 2014", 3 pgs.
"Australian Application Serial No. 2011296356, Amendment filed Jun. 3, 2014", 21 pgs.
"Australian Application Serial No. 2011296356, First Examiner Report mailed Jun. 10, 2014", 7 pgs.
"Australian Application Serial No. 2011296356, Response filed Jun. 11, 2015 to First Examiner Report mailed Jun. 10, 2014", 20 pgs.
"Bio-Gel P Polyacrylamide Gel", Instruction Manual, downloaded on Jun. 20, 2012 from [Online] retrieved from internet: <www.bio-rad.com/webmaster/pdfs/9154_Bio-Gel P.pdf>, 1-14.
"BioCUE™ Platelet Concentration System", (Jun. 2010), 2 pgs.
"Canadian Application Serial No. 2,772,067, Office Action mailed Jan. 8, 2015", 3 pgs.
"Canadian Application Serial No. 2,772,067, Office Action mailed Nov. 24, 2015", 3 pgs.
"Canadian Application Serial No. 2,772,067, Response filed Mar. 1, 2016 to Office Action mailed Nov. 24, 2015", 7 pgs.
"Canadian Application Serial No. 2,772,067, Response filed Jul. 8, 2015 to Office Action mailed Jan. 8, 2015", 24 pgs.
"Canadian Application Serial No. 2,772,069, Office Action mailed Sep. 16, 2015", 3 pgs.
"Canadian Application Serial No. 2,810,202, Office Action mailed Jul. 2, 2015", 5 pgs.
"Canadian Application Serial No. 2,810,202, Response filed Dec. 30, 2015 to Office Action mailed Jul. 2, 2015", 19 pgs.
"Canadian Application Serial No. 2,810,202, Voluntary Amendment filed Jan. 13, 2014", 12 pgs.
"Canadian Application Serial No. 2,905,552, Voluntary Amendment filed Sep. 11, 2015".
"Canadian Application Serial No. 2,906,310, Voluntary Amendment filed Sep. 14, 2015", 2 pgs.
"Caps for Corning® and Costar® Plastic Labware", Technical Bulletin, (Dec. 2008), 2 pgs.
"Cell Isolation Techniques, Methods and Materials, Working with Enzymes", Worthington Biochemical Corp, (2004), 9 pgs.
"Cell Isolation Theory, Tissue Types", Worthington Biochemical Corp, (2004), 5 pgs.
"Centrifuge Tubes", Corning Costar, (1996/1997), 76-77.
"Chinese Application Serial No. 201080019707.7, Office Action mailed Jun. 30, 2014", in English, 7 pgs.
"Chinese Application Serial No. 2010800428565, Non Final Office Action mailed Jan. 22, 2013", W/ English Translation, 10 pgs.
"Chinese Application Serial No. 2010800428565, Non Final Office Action mailed Feb. 14, 2014", W/ English Translation, 5 pgs.
"Chinese Application Serial No. 2010800428565, Non Final Office Action mailed Sep. 10, 2013", W/ English Translation, 10 pgs.
"Chinese Application Serial No. 2010800428565, Response filed Apr. 29, 2014 to Non Final Office Action mailed Feb. 14, 2014", W/ English Claims, 7 pgs.
"Chinese Application Serial No. 2010800428565, Response filed Aug. 6, 2013 to Non Final Office Action mailed Jan. 22, 2013", W/ English Claims, 9 pgs.
"Chinese Application Serial No. 2010800428565,Response filed Nov. 25, 2013 to Non Final Office Action mailed Sep. 10, 2013", W/ English Claims, 10 pgs.

(56) References Cited

OTHER PUBLICATIONS

"Chinese Application Serial No. 2010800447744, Decision on rejection mailed Nov. 15, 2014", W/ English Translation, 10 pgs.
"Chinese Application Serial No. 2010800447744, Notification of Reexamination mailed Feb. 23, 2016", W/ English Translation, 9 pgs.
"Chinese Application Serial No. 2010800447744, Office Action mailed Jan. 31, 2013", W/ English Translation, 12 pgs.
"Chinese Application Serial No. 2010800447744, Office Action mailed Apr. 30, 2014", Without English Translation, 5 pgs.
"Chinese Application Serial No. 2010800447744, Office Action mailed Oct. 22, 2013", 10 pgs.
"Chinese Application Serial No. 2010800447744, Response filed Jan. 6, 2014 to Office Action mailed Oct. 22, 2013", with English translation of claims, 27 pgs.
"Chinese Application Serial No. 2010800447744, Response filed Feb. 19, 2015 to Decision on rejection mailed Nov. 15, 2014", (W/ English Translation), 13 pgs.
"Chinese Application Serial No. 2010800447744, Response filed Apr. 11, 2016 to Notification of Reexamination mailed Feb. 23, 2016", with English translation of claims, 23 pgs.
"Chinese Application Serial No. 2010800447744, Response filed Jun. 17, 2013 to Office Action mailed Jan. 31, 2013", 8 pgs.
"Chinese Application Serial No. 2010800447744, Response filed Jul. 15, 2014 to Office Action mailed Apr. 30, 2014", with English translation of claims, 25 pgs.
"Chinese Application Serial No. 201280030026.X, Office Action mailed Nov. 21, 2014", w/ English Translation, 27 pgs.
"Chinese Application Serial No. 201480027541.1, Voluntary Amendment mailed May 5, 2016", W/ English Claims, 15 pgs.
"Clotalyst® Autologous Clotting Factor", "Would you like to have an autologous thrombin for rapid clotting and haemostasis?" Biomet Biologics, (Jan. 2007), 16 pgs.
"Corning® 15 and 50 ml Centrifuge Tubes", Life Sciences. Corning Incorporated., (Jun. 2005), 2 pgs.
"Cytori Celution Cell Concentrate Device", Exhibit 14, 501(k) Summary, FDA approval K060482, (Sep. 28, 2006), 7 pgs.
"European Application No. 09715775.4, Non Final Office Action mailed Apr. 26, 2011", 5 pgs.
"European Application No. 09715775.4, Preliminary Amendment filed Sep. 22, 2010", 9 pgs.
"European Application No. 09715775.4,Response filed Oct. 12, 2011 to Non Final Office Action mailed Apr. 26, 2011", 20 pgs.
"European Application No. 09715775.4,Supplemental Preliminary Amendment filed Nov. 17, 2010", 12 pgs.
"European Application Serial No. 10712677.3, Examination Notification Art. 94(3) mailed Jun. 5, 2013", 5 pgs.
"European Application Serial No. 10754379.5, Examination Notification Art. 94(3) mailed Aug. 16, 2013", 5 pgs.
"European Application Serial No. 10754379.5, Examination Notification Art. 94(3) mailed Dec. 15, 2014", 4 pgs.
"European Application Serial No. 10754379.5, Office Action mailed Apr. 3, 2012", 2 pgs.
"European Application Serial No. 10754379.5, Response filed Feb. 17, 2014 to Examination Notification Art. 94(3) mailed Aug. 16, 2013", 13 pgs.
"European Application Serial No. 10754379.5, Response filed Apr. 13, 2015 to Examination Notification Art. 94(3) mailed Dec. 15, 2014", 8 pgs.
"European Application Serial No. 10754379.5, Response filed Sep. 28, 2012 to Office Action mailed Apr. 3, 2012", 11 pgs.
"European Application Serial No. 10754613.7, Communication Pursuant to Article 94(3) EPC mailed Sep. 16, 2013", 4 pgs.
"European Application Serial No. 10754613.7, Communication Pursuant to Article 94(3) EPC mailed Nov. 13, 2015", 4 pgs.
"European Application Serial No. 10754613.7, Response filed Mar. 14, 2014 to Communication Pursuant to Article 94(3) EPC mailed Sep. 16, 2013", 15 pgs.
"European Application Serial No. 10754613.7, Response filed Mar. 15, 2016 to Communication Pursuant to Article 94(3) EPC mailed Nov. 13, 2015", 26 pgs.
"European Application Serial No. 10754613.7, Response filed Oct. 1, 2012 to Communication pursuant to Rules 161(1) and 162 EPC mailed Mar. 4, 2012", 15 pgs.
"European Application Serial No. 11754786.9, Examination Notification Art. 94(3) mailed Aug. 10, 2014", 5 pgs.
"European Application Serial No. 12195882.1, Extended European Search Report mailed Jan. 31, 2013", 5 pgs.
"European Application Serial No. 12195882.1, Non Final Office Action mailed Jun. 30, 2014", 4 pgs.
"European Application Serial No. 12195882.1, Response filed Sep. 11, 2013 to Extended European Search Report mailed Jan. 31, 2013", 16 pgs.
"European Application Serial No. 12195882.1, Response filed Oct. 29, 2014 to Non Final Office Action mailed Jun. 30, 2014", 18 pgs.
"European Application Serial No. 13165543.3, Extended European Search Report mailed Jul. 1, 2013", 6 pgs.
"European Application Serial No. 13165543.3, Non Final Office Action mailed Jun. 27, 2014", 5 pgs.
"European Application Serial No. 13165543.3, Response filed Jan. 14, 2014 to Extended European Search Report mailed Jul. 1, 2013", 11 pgs.
"European Application Serial No. 13165543.3, Response filed Oct. 24, 2014 to Non Final Office Action mailed Jun. 27, 2014", 6 pgs.
"European Application Serial No. 14707069.2, Response filed May 23, 2016 to Communication pursuant to Rules 161(1) and 162 EPC mailed Nov. 12, 2015", 12 pgs.
"European Application Serial No. 14707909.9, Communication Pursuant to Article 94(3) EPC mailed Jul. 22, 2016", 9 pgs.
"European Application Serial No. 14707909.9, Preliminary Amendment filed on May 13, 2016", 14 pgs.
"European Application Serial No. 14707909.9, Response filed May 13, 2016 to Communication pursuant to Rules 161(1) and 162 EPC mailed Nov. 3, 2015", 14 pgs.
"European Application Serial No. 14709014.6, Office Action mailed Nov. 19, 2015", 2 pgs.
"European Application Serial No. 14709803.2, Response filed May 16, 2016 to Communication pursuant to Rules 161(1) and 162 EPC mailed Nov. 5, 2015", 14 pgs.
"European Application Serial No. 14714491.9, Response filed Aug. 1, 2016 to Communication Pursuant to Rules 161 and 162 EPC mailed Jan. 21, 2016", 11 pgs.
"European Application Serial No. 14724817.3, Office Action mailed Oct. 27, 2015", 2 pgs.
"European Application Serial No. 14724817.3, Response filed May 6, 2016 to Communication pursuant to Rules 161(1) and 162 EPC mailed Oct. 27, 2015", 13 pgs.
"European Application Serial No. 14729994.5, Response filed May 9, 2016 to Communication pursuant to Rules 161(1) and 162 EPC mailed Oct. 30, 2015", 14 pgs.
"European Application Serial No. 15184504.7, Extended European Search Report mailed Oct. 20, 2015", 7 pgs.
"Fibrostik™ Plasma Concentrator", Attention Operating Surgeon, Cell Factor Technologies, Inc., (Jul. 2003), 2 pgs.
"Frequently Asked Questions, 1. Kits, 2. Enzymes", Worthington Biochemical Corp, (2003), 3 pgs.
"GPS® III Platelet Separation System, Leadership through Technology", Biomet Biologics, Inc, (Jul. 2007), 8 pgs.
"Hemocor HPH® Hemoconcentrator", Minntech® Filtration Technologies Group, Minntech Corporation (2004), <http://www.minntech.com/ftg/products/hph/index.html>, (Jul. 15, 2004), 2 pgs.
"Increasing bone graft bioactivity through reproducible concentrations of natural growth factors", Symphony II Platelet Concentrate System/PCS brochure, (Jan. 2003), 8 pgs.
"International Application Serial No. PCT/US2003/016506, International Search Report mailed Oct. 13, 2003", 2 pgs.
"International Application Serial No. PCT/US2007/012587, International Search Report mailed Nov. 6, 2007", 2 pgs.
"International Application Serial No. PCT/US2008/004687, International Preliminary Report on Patentability mailed Aug. 13, 2009", 19 pgs.

(56) References Cited

OTHER PUBLICATIONS

"International Application Serial No. PCT/US2008/004687, International Search Report mailed Jul. 2, 2008", 3 pgs.
"International Application Serial No. PCT/US2008/004687, Written Opinion mailed Mar. 17, 2009", 5 pgs.
"International Application Serial No. PCT/US2008/004687, Written Opinion mailed Jul. 2, 2008", 5 pgs.
"International Application Serial No. PCT/US2009/035541, International Preliminary Report on Patentability mailed Aug. 3, 2010", 8 pgs.
"International Application Serial No. PCT/US2009/035541, International Search Report mailed Jun. 16, 2009", 3 pgs.
"International Application Serial No. PCT/US2009/035541, Written Opinon mailed Jun. 16, 2009", 7 pgs.
"International Application Serial No. PCT/US2009/035564, International Preliminary Examination Report mailed Aug. 31, 2010", 6 pgs.
"International Application Serial No. PCT/US2009/035564, International Search Report mailed Jul. 3, 2009", 3 pgs.
"International Application Serial No. PCT/US2009/035564, Written Opinion mailed Jul. 3, 2009", 5 pgs.
"International Application Serial No. PCT/US2010/029957, International Preliminary Report on Patentability mailed Oct. 13, 2011", 10 pgs.
"International Application Serial No. PCT/US2010/029957, International Search Report mailed Jul. 30, 2010", 6 pgs.
"International Application Serial No. PCT/US2010/029957, Written Opinion mailed Jul. 30, 2010", 9 pgs.
"International Application Serial No. PCT/US2010/041942, International Preliminary Report on Patentability mailed Jan. 26, 2012", 9 pgs.
"International Application Serial No. PCT/US2010/041942, International Search Report mailed Oct. 8, 2010", 3 pgs.
"International Application Serial No. PCT/US2010/041942, Written Opinion mailed Oct. 8, 2010", 8 pgs.
"International Application Serial No. PCT/US2010/046821, International Preliminary Report on Patentability mailed Mar. 8, 2012", 6 pgs.
"International Application Serial No. PCT/US2010/046821, International Search Report mailed Jul. 22, 2011", 4 pgs.
"International Application Serial No. PCT/US2010/046821, Written Opinion mailed Jul. 22, 2011", 4 pgs.
"International Application Serial No. PCT/US2011/031954, International Search Report mailed Aug. 9, 2011", 4 pgs.
"International Application Serial No. PCT/US2011/031954, Written Opinion mailed Aug. 9, 2011", 9 pgs.
"International Application Serial No. PCT/US2011/045290, International Search Report mailed Nov. 7, 2011", 5 pgs.
"International Application Serial No. PCT/US2011/045290, Written Opinion mailed Nov. 7, 2011", 5 pgs.
"International Application Serial No. PCT/US2012/034104, International Preliminary Report on Patentability mailed Oct. 31, 2013", 7 pgs.
"International Application Serial No. PCT/US2012/034104, International Search Report mailed Oct. 29, 2012", 5 pgs.
"International Application Serial No. PCT/US2012/034104, Written Opinion mailed Oct. 29, 2012", 6 pgs.
"International Application Serial No. PCT/US2013/056793, International Preliminary Report on Patentability mailed Mar. 12, 2015", 8 pgs.
"International Application Serial No. PCT/US2013/056793, International Search Report mailed Dec. 5, 2013", 3 pgs.
"International Application Serial No. PCT/US2013/056793, Written Opinion mailed Dec. 5, 2013", 6 pgs.
"International Application Serial No. PCT/US2014/016384, International Preliminary Report on Patentability mailed Sep. 24, 2015", 16 pgs.
"International Application Serial No. PCT/US2014/016384, International Search Report mailed Oct. 9, 2014", 10 pgs.
"International Application Serial No. PCT/US2014/016384, Written Opinion mailed Oct. 9, 2014", 14 pgs.
"International Application Serial No. PCT/US2014/016421, International Preliminary Report on Patentability mailed Sep. 24, 2015", 16 pgs.
"International Application Serial No. PCT/US2014/016421, International Search Report mailed Jul. 24, 2014", 8 pgs.
"International Application Serial No. PCT/US2014/016421, Written Opinion mailed Jul. 24, 2014", 14 pgs.
"International Application Serial No. PCT/US2014/016895, International Preliminary Report on Patentability mailed Sep. 24, 2015", 16 pgs.
"International Application Serial No. PCT/US2014/016895, International Search Report mailed Jul. 24, 2014", 9 pgs.
"International Application Serial No. PCT/US2014/016895, Written Opinion mailed Jul. 24, 2014", 14 pgs.
"International Application Serial No. PCT/US2014/016900, International Preliminary Report on Patentability mailed Sep. 24, 2015", 9 pgs.
"International Application Serial No. PCT/US2014/016900, International Search Report mailed May 12, 2014", 5 pgs.
"International Application Serial No. PCT/US2014/016900, Written Opinion mailed May 12, 2014".
"International Application Serial No. PCT/US2014/021707, International Preliminary Report on Patentability mailed Sep. 24, 2015", 16 pgs.
"International Application Serial No. PCT/US2014/021707, International Search Report mailed Jul. 24, 2014", 8 pgs.
"International Application Serial No. PCT/US2014/021707, Written Opinion mailed Jul. 24, 2014", 14 pgs.
"International Application Serial No. PCT/US2014/023091, International Preliminary Report on Patentability mailed Sep. 24, 2015", 11 pgs.
"International Application Serial No. PCT/US2014/023091, International Search Report mailed Oct. 9, 2014", 7 pgs.
"International Application Serial No. PCT/US2014/023091, Written Opinion mailed Oct. 9, 2014", 9 pgs.
"International Application Serial No. PCT/US2014/028942, International Preliminary Report on Patentability mailed Sep. 24, 2015", 15 pgs.
"Japanese Application Serial No. 2010-503066, Office Action mailed Jan. 22, 2013", w/ English Translation, 17 pgs.
"Japanese Application Serial No. 2012-503768, Office Action mailed May 20, 2014", w/ English Translation, 5 pgs.
"Japanese Application Serial No. 2012-520742, Office Action mailed Sep. 9, 2014", w/ English Translation, 6 pgs.
"Japanese Application Serial No. 2012-526988, Office Action mailed Oct. 1, 2013", W/ English Translation, 4 pgs.
"Japanese Application Serial No. 2012-526988, Response filed Mar. 3, 2014 to Office Action mailed Oct. 1, 2013", W/ English Claims, 21 pgs.
"Japanese Application Serial No. 2012-526990, Examiners Decision of Final Refusal mailed Jun. 3, 2016", W/ English Translation, 6 pgs.
"Japanese Application Serial No. 2012-526990, Office Action mailed Jun. 26, 2015", (W/ English Translation), 12 pgs.
"Japanese Application Serial No. 2012-526990, Office Action mailed Aug. 5, 2014", 4 pgs.
"Japanese Application Serial No. 2012-526990, Response filed Dec. 5, 2014 to Office Action mailed Aug. 5, 2014", 19 pgs.
"Japanese Application Serial No. 2012-526990, Response filed Dec. 25, 2015 to Office Action mailed Jun. 26, 2015", (W/ English Translation), 14 pgs.
"Japanese Application Serial No. 2013-174962, Notice of Reasons for Rejection mailed Jul. 31, 2015", W/ English Translation, 10 pgs.
"Japanese Application Serial No. 2013-174962, Office Action mailed Sep. 12, 2014", 6 pgs.
"Japanese Application Serial No. 2013-174962, Response filed Mar. 12, 2015 to Office Action mailed Sep. 12, 2014", (W/ English Translation), 18 pgs.
"Japanese Application Serial No. 2013-174962, Response filed Oct. 30, 2015 to Notice of Reasons for Rejection mailed Jul. 31, 2015", W/ English Claims, 16 pgs.

(56) References Cited

OTHER PUBLICATIONS

"Japanese Application Serial No. 2013-527119, Office Action mailed Mar. 1, 2016", W/ English Translation, 12 pgs.
"Japanese Application Serial No. 2013-527119, Office Action mailed Jun. 12, 2015", (W/ English Translation), 11 pgs.
"Japanese Application Serial No. 2013-527119, Response filed Aug. 1, 2016 to Office Action mailed Mar. 1, 2016", 13 pgs.
"Japanese Application Serial No. 2013-527119, Response filed Oct. 1, 2015 to Office Action mailed Jun. 12, 2015", 12 pgs.
"Japanese Application Serial No. 2014-024420, Preliminary Notice of Reasons for Rejection mailed Feb. 24, 2015", w/ English Translation, 15 pgs.
"Knee Cartilage Implantation Carticel™, Autologous Cultured Chondrocyte Implantation", The Sports Medicine Center, [Online]. Retrieved from the Internet: <http://www.orthoassociates.com/carticel.htm>, (Apr. 6, 2006), 7 pgs.
"Letter CryoSeal FS System. Vaccines, Blood & Biologics", FDA U.S. Food and Drug Administation., http://www.fda.gov/BiologicsBioodVaccines/BioodBioodProducts/ApprovedProducts/Premark et ApprovalsPMAs/ucm091631.htm, (Jul. 26, 2007), 21 pgs.
"MarrowStim™ Concentration Kit Peripheral Arterial Disease (PAD) Study", Retriewed From Intenet : <http://www.biomet.com/patients/clinical recruitment padstudy.cfm>, (Jul. 2, 2009), 2 pgs.
"MarrowsTim™ Concentration System", Biomet Biologics, Inc, (Feb. 15, 2008), 20 pgs.
"Medical Applications: Blood Filtration", Minntech® Filtration Technologies Group, Minntech Corporation (2004), <http://www.minntech.com/ftg/industries/medical/blood_filter.html>, (Jul. 15, 2004), 1 pg.
"Minivalve international: duckbill valves—du 054.001 sd", [Online]. Retrieved from the Internet: <http://www.minivalve.com/htm/DV054.htm>, 1 pg.
"Momentive Silopren*LSR 2050", (Jun. 30, 2014), 3 pg.
"Platelet Rich Plasma (PRP)". The Stone Clinic, (May 2006), 2 pgs.
"Prosys PRP Kit", Tozai Holdings, Inc. EC21 Global B2B Marketplace, Retrieved From Internet : <http://www.ec21.com/product-details/Prosys-PRP-Kit--5467061.html Printed from Web>, (Jul. 18, 2011), 5 pgs.
"Renaflo® II Hemofilter", Minntech® Filtration Technologies Group, Minntech Corporation (2004), <http://www.minntech.com/ftg/products/renaflo/index.html>, (Jul. 15, 2004), 2 pgs.
"Sigma-Aldrich® Alkaline Phosphatase (Procedure No. 85), drug fact sheet", Sigma-Aldrich, (2003), 1-2.
"SmartPrep PRP-20 Procedure Pack—Instructions for Use", Harvest, 12 pgs.
"ThermoGenesis Corp. to Supply Autologous Thrombin Kits to Biomet, Inc", noblood: Transfusion Alternatives Patient Blood Mangement, [Online]. Retrieved from the Internet: <URL: http://noblood.org/forum/threads/2128-ThermoGenesis-Corp-to-Supply-Autologous-Thrombin-Kits-to-Biomet-Inc>, (Apr. 5, 2005), 3 pgs.
"Trypsinizing cells", Bart's Cook Book, 1 pg.
"Vernay Product Information Sheet, Umbrella Check Valve", Part No. V251010200, (Jul. 2013), 2 pgs.
Aaron, "Stimulation of Experimental Endochondral Ossification by Low-Energy Pulsing Electromagnetic Fields", Journal of Bone and Mineral Research, (1989), 227-233.
Aaron, et al., "Therapeutic Effects of Electromagnetic Fields in the Stimulation of Connective Tissue Repair", Journal of Cellular Biochemistry, (1993), 42-46.
Aaron, et al., "Upregulation of basal TGFb1 levels by EMF coincident with chondrogenesis—implications for skeletal repair and tissue engineering", Journal of Orthopaedic Research, (2002), 233-240.
Aaron, Roy K., et al., "Acceleration of Experimental Endochondral Ossification by Biophysical Stimulation of the Progenitor Cell Pool", Journal of Orthopaedic Research, (1996), 582-589.
Aaron, Roy K., et al., "Power Frequency Fields Promote Cell Differentiation Coincident With an Increase in Transforming Growth Factor-?1 Expression", Bioelectromagnetics, (1999), 453-458.
Andia, Isabel, et al., "Platelet-rich plasma for managing pain and inflammation in osteoarthritis", Nature Reviews Rheumatology, vol. 9, No. 12., (Oct. 1, 2013), 721-730.
Badiavas, Evangelos V., et al., "Treatment of Chronic Wounds With Bone Marrow-Derived Cells", Arch Dermatol. 139, (Apr. 2003). 510-516.
Bang, N U. et al., "Plasma Protein Requirements for Human Platelet Aggregation", Acad Sci, 201, (1972), 280-299.
Bendele, Alison M, et al., "Combination Benefit of Treatment With the Cytokine Inhibitors Interleukin-1 Receptor Antagonist and Pegylated Soluble Tumor Necrosis Factor Receptor Type I in Animal Models of Rheumatoid Arthritis", Arthritis & Rheumatism, J.B. Lippincott vol. 43, No. 12, (Dec. 1, 2000), 2648-2659.
Berguer, R, et al., "Warning: fatal reaction to the use of fibrin glue in deep hepatic wounds. Case reports", J Trauma 31, (1991), 408-411.
Berruyer, M, et al., "Immunization by bovine thrombin used with fibrin glue during cardiovascular operations. Development of thrombin and factor V inhibitors", J Thorac Cardiovasc Sura 105, (1993), 892-7.
Boomgaard, et al., "Pooled Platelet Concentrates Prepared by the Platelet-Rich-Plasma Method and Filtered with Three Different Filters and Stored for 8 Days", Vox Sanq, vol. 68, (Feb. 1995), 82-89.
Brodke, et al., "Bone Grafts Prepared with Selective Cell Retention Technology Heal Canine Segmental Defects as Effectively as Autograft", SCR-Enriched Bone Grafts Heal Canine Segmental Defects, Journal of Orthopaedic Research, (May 2006), 857-866.
Carpenter, et al., "Long-term storage of proteins", Current Protocols in Protein Science, (2002), 6 pgs.
Carpenter, et al., "Rationale Design of stable protein formulations-theory and practice", Rationale design of stable lyophilized protein formulations: theory and practice., (2002), 109-133.
Casali, B, et al., "Fibrin glue from single-donation autologous plasmapheresis", Transfusion 32, (1992), 641-643.
Clayden, J D, et al., "Improved segmentation reproducibility in group tractography using a quantitative tract similarity measure", Neuroimage, Academic Press, Orlando, FL, US vol. 33, No. 2, (Nov. 1, 2006), 482-492.
Collier, B S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda Blood, vol. 47, No. 5, (May 1976).
Connolly, John, et al., "Development of an Osteogenic Bone-Marrow Preparation", The Journal of Bone and Joint SurQery, Incorporated. vol. 71-A, No. 5, (Jun. 1989), 684-691.
Connolly, John F., "Injectable Bone Marrow Preparations to Stimulate Osteogenic Repair", Clinical Orthopaedics and Related Research 313, (Apr. 1995), 8-18.
Dallari, et al., "In Vivo Study on the Healing of Bone Defects Treated with Bone Marrow Stromal Cells, Platelet-Rich Plasma, and Freeze-Dried Bone Allografts, Alone and in Combination", Healing of Bone Defects, Journal of Orthopaedic Research, (May 2006), 877-888.
Dawson, J, et al., "Effects of soluble interleukin-1 type II receptor on rabbit antigen-induced arthritis: Clinical, biochemical and histological assessment", Rheumatology (Oxford) vol. 38, No. 5, (May 5, 1999), 401-406.
Dayer, Jean-Michel, et al., "Adipose tissue has anti-inflammatory properties: focus on IL-1 receptor antagonist (IL-1Ra)", Annals of the New York Academy of Sciences, vol. 1069, (Jun. 2006), 444-53.
De Ugarte, et al., "Comparison of Multi-Lineage Cells from Human Adipose Tissue and Bone Marrow", Cells Tissues Organs 174, (2003), 101-109.

(56) References Cited

OTHER PUBLICATIONS

De Ugarte, et al., "Differential Expression of Stem Cell Mobilization-Associated Molecules on Multi-Lineage Cells from Adipose Tissue and Bone Marrow", Immunology Letters 89, (2003), 267-270.

De Wit, et al., "Experiments on the Preparation of Blood Components with the IBM 2991 Blood Cell Processor", Vox Sang. 29, (Feb. 10, 1975), 352-362.

Delrossi, A, et al., "Platelet-rich plasma reduces postoperative blood loss after cardiopulmonary bypass", J Thorac Cardiovasc Sura 100, (Aug. 1990), 281-285.

Depalma, L, "The preparation of fibrinogen concentrate for use as fibrin glue by four different methods", Transfusion vol. 33, No. 9, (1993), 717-720.

Deugarte, M D, et al., "Future of Fat as Raw Material for Tissue Regeneration", Lippincott Williams & Wilkins, Inc., (2007), 215-219.

Dimuzio, Paul, et al., "Development of a Tissue-Engineered Bypass Graft Seeded with Stem Cells", Vasucular, vol. 14, No. 6, (2006), 338-342.

Dinarello, C, "Interleukin-1 and Interleukin-1 Antagonism", Blood, vol. 77, No. 8, (Apr. 1991), 1627-1652.

Edlich, Richard F. et al., "Surgical Devices in Wound Healing Management", In Wound Healing: Biochemical & Clinical Aspects 1st ed., vol. Philadelphia: W.B. Saunders Company, (1992), 581-601.

Ehricke, H H, et al., "Visualizing MR diffusion tensor fields by dynamic fiber tracking and uncertainty mapping", Computers and Graphics, Elsevvier vol. 30, No. 2, (Apr. 1, 2006), 255-264.

Epstein, G H, et al., "A new autologous fibrinogen-based adhesive for otologic surgery", Ann Otol Rhinol Laryngol 95, (May 25-26, 1985), 40-45.

Feige, U, et al., "Anti-interleukin-1 and anti-tumor necrosis factor-alpha synergistically inhibit adjuvant arthritis in Lewis rats", Cmls Cellular and Molecular Li Fe Sciences, Bi Rkhauser Verlag, Heidelberg, DE, vol. 57, No. 10, (Sep. 1, 2000), 1457-1470.

Fini, et al., "Effects of pulsed electromagnetic fields on articular hyaline cartilage: review of experimental and clinical studies", Biomedicine and Pharmacotherapy, Elsevier, FR, vol. 59, No. 7, (Aug. 1, 2005), 388-394.

Fraser, John K. et al., "Plasticity of human adipose stem cells toward endothelial cells and cardiomyocytes", Nature Clinical Practice Cardiovascular Medicine, vol. 3, Supplement 1, (Mar. 2006), S33-S37.

Friesen, Robert, et al., "Blood Conservation During Pediatric Cardiac Surgery: Ultrafiltration of the Extracorporeal Circuit Volume After Cardiopulmonary Bypass", Anesth, Analg, (1993), 702-707.

Galois, et al., "Cartilage Tissue Engineering: State-of-the-Art and Future Approaches", Pathol Bioi (Paris), 53—Abstract only, (Dec. 2005), 2 pgs.

Gerald, Marx, "Mechanism of Fibrin Coagulation Based on Selective, Cation-Driven, Protofibral Association", Biopolymers, vol. 27, (1988), 763-774.

Gibble, et al., "Fibrin glue: the perfect operative sealant". Transfusion, 1990, vol. 30, No. 8., (1990), 741-747.

Gimble, Jeffrey M, "Adipose-Derived Stem Cells for Regenerative Medicine", Circulation Research American Heart Association, Inc., (May 11, 2007), 1249-1260.

Gomillion, Cheryl T, et al., "Stem cells and adipose tissue engineering", Biomaterials 27, Science Direct Elsevier, (2006), 6052-6063.

Grove, et al., "Plasticity of Bone Marrow-Derived Stem Cells", Stem Cells: Concise Review, (Jan. 2004), 487-500.

Guilak, Farshid, et al., "Adipose-derived adult stem cells for caltilage tissue engineering", Biorheology 41, (2004), 389-399.

Harris, E. L. V, et al., "Protein Purification Methods—A Practical Approach", Clarification and Extraction, (1989), 7 pgs.

Hartman, A. R. et al., "Autologous whole plasma fibrin gel. Intraoperative procurement", Arch Surg 127, (Mar. 1992), 357-359.

Hattori, et al., "Osteogenic Potential of Human Adipose Tissue-Derived Stromal Cells as an Alternative Stem Cell Source", Cells Tissues Organs, (2004), 2-12.

Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.

Hennis, H L, et al., "Infectious disease risks of fibrin glue [Letter]", Ophthalmic Sura 23, (Sep. 1992), 1 pg.

Hernigou, et al., "Percutaneous Autologous Bone-Marrow Grafting for Nonunions. Influence of the Number and Concentration of Progenitor Cells", Journal of Bone & Joint Surgery, (Jul. 2005), 1430-1437.

Hiromasa, Mitsuhata, et al., "An Anaphylactic Reaction to Topical Fibrin Glue", Anesthesiology, vol. 81, No. 4, (Oct. 1994), 1074-1077.

Hom. D. et al., "Promoting Healing with Recombinant Human Platelet-Derived Growth Factor-BB in a Previously Irradiated Problem Wound", The Laryngoscope, vol. 113, (Sep. 2003), 1566-1571.

Hood, Andrew G, et al., "Perioperative Autologous Sequestration III: A New Physiologic Glue with Wound Healing Properties", (Jan. 1993), 126-129.

Ishida, et al., "Platelet-Rich Plasma With Biodegradable Gelatin Hydrogel Promotes Rabbit Meniscal Tissue Regeneration", 52nd Annual Meeting of the Orthopaedic Research Society Paper No. 1035, (2006), 1 pg.

Jackson, C M, et al., "Blood coagulation", Annu Rev Biochem 49: 765-811, (1980), 22 pgs.

Jayadev, Suprya, "Trypsinization of Adherent Cells", (Aug. 8, 1991), 1 pg.

Johnstone, et al., "Autologous Mesenchymal Progenitor Cells in Articular Cartilage Repair", Clinical Orthopaedics and Related Research 367S:, (Oct. 1999), S156-S162.

Jones, D K, et al., "Confidence mapping in diffusion ensor magnetic resonance imaging tractography using a bootstrap approach", Magnetic Resonance in Medicine Wiley USA, vol. 53 , No. 5, (May 2005), 1143-1149.

Jorgensen, et al., "Stem Cells for Repair of Cartilage and Bone: The Next Challenge in Osteoarthritis and Rheumatoid Arthritis", Annals of Rheumatic Diseases, (Aug. 2000), 5 pgs.

Karpatkin, S., "Heterogeneity of Human Platelets. VI., Correlation of Platelet Function with Platelet Volume", Blood, vol. 51, No. 2, (Feb. 1978), 307-316.

Kim, Seon Hee, et al., "Ex vivo gene delivery of II-1 Ra and soluble TNF receptor confers a distal synergistic therapeutic effect in antigen-induced arthritis", Molecular Therapy, vol. 6, No. 5, (Nov. 1, 2002), 591-600.

Kim, Sun Jin, et al., "Development of a novel sustained release formulation of recombinant human growth homrone using sodium hyaluronate microparticles". Journal of Controlled Release, 2005, vol. 104 (2005), 323-335.

Kimble, Robert B. et al., "Simultaneous block of interleukin-1 and tumor necrosis factor is required to completely prevent bone loss in the early postovariectomy period", Endocrinology, The Endocrine Society, US, vol. 136, No. 7—Abstract, (Jul. 1, 1995), 1 pg.

Kitazawa, R, et al., "Interleukin-1 Receptor Antagonist and Tumor Necrosis Factor Binding Protein Decrease Osteoclast Formation and Bone Resorption in Ovariectomized Mice", Journal of Clinical Investigation, American Society for Clinical Investigation, US, vol. 94, No. 6, (Dec. 1, 1994), 2397-2406.

Kjaergard, H. K, et al., "A simple method of preparation of autologous fibrin glue by means of ethanol", Surg Gynecol Obstet 175, (1992), 72-3.

Kjaergard, H. K. "Preparation of autologous fibrin glue from pericardial Blood", Ann Thorac Sur 55, (1993), 543-4.

Kohsaka, Hitoshi, "Gene Transfer Therapy for Rheumatoid Arthritis", Japanese Journal of Clinical Medicine, No. 63, No. 9, (2005), 8 pgs.

Kuderma, H, et al., "Die klinische Anwendung der Klebung van Nervenanastomosen mit Gerinnungssubstanzen bei der Rekonstruction verletzter peripherer Nerven", Wein Klin Wochenschr 87—Not in English, (Aug. 15, 1975), 6 pgs.

(56) References Cited

OTHER PUBLICATIONS

Kumar. Vijay, et al., "Autologous Thrombin: Intraoperative Production From Whole Blood", Journal of American Society of Extra-Corporeal Technology. JECT, 40, (2008), 94-98.

Kumar, Vijay, et al., "Stability of Human Thrombin Produced From 11 ml of Plasma Using the Thrombin Processing Device", Journal of American Society of Extra-Corporeal Technology JECT, 37, (Mar. 2005), 390-395.

Kumar, Vijay, et al., "Whole Blood Thrombin: Development of a Process for Intra-Operative Production of Human Thrombin", Journal of American Society of Extra-Corporeal Technology JECT, 39, (Apr. 2007), 18-23.

Kwon, Young-Bae, et al., "Topical application of epidermal growth factor accelerates wound healing by myofibroblast proliferation and collagen synthesis in rat", Journal of Vetrinary Science 7(2), (2006), 105-109 pgs.

Kyosti Laitakari, M D, et al., "Autologous and Homologous Fibrinogen Sealants: Adhesive Strength", Laryngoscope vol. 99, (Sep. 1989), 974-976.

Laplante, Ben L, et al., "Spine osteoarthritis", PM&R, vol. 4, (2012), S28-S36.

Lasher, Lisa, "My Experience with PRP", PowerPoint presentation, <http://www.cellfactortech.com/global_products.cfm>, (Sep. 16, 2005), 35 pgs.

Lendeckel, Stefan, et al., "Autologous stem cells (adipose) and fibrin glue used to treat widespread traumatic calvarial defects: case report", Journal of Cranio-Maxillofacial Surgery (2004) European Association for Cranio-Maxillofacial Surgery, (2004), 370-373.

Lerner, R. et al., "Current status of surgical adhesives", J Surg Res 48, (Feb. 1990), 165-80.

Longas, Maria O, "An Improved Method for the Purification of Human Fibrinogen", J. Biochem vol. 11, (1980), 559-564.

Lori, N F, et al., "Diffusion tensor fiber tracking of human brain connectivity: acquisition methods, reliability analysis and biological results", NMR in Biomedicine Wiley UK, vol. 15, No. 7-8, (Nov. 2002), 493-515.

Lu, X. et al., "Bone Marrow Mesenchymal Stem Cells: Progress in Bone/Cartilage Defect Repair", 19(1) Abstract, (Jan. 2002), 2 pgs.

Lucarelli. E. et al., "Platelet-derived growth factors enhance proliferation of human stromal stem cells", Biomaterials, vol. 24, (2003), 3095-3100.

Marx, Gerard, et al., "Heat Denaturation of Fibrinogen to Develop a Biomedical Matrix", Journal of Biomedical Materials Research Part B: Applied Biomaterials, (Apr. 2007), 49-57.

Masri, Marwan A. et al., "Isolation of Human Fibrinogen of High Purity and in High Yield Using Polyethylene Glycol 1000", Thromb Haemostas (Struttgart) vol. 49 (2), (1983), 116-119.

Matras, Helene, "Fibrin Seal: The State of the Art", Journal of Oral Maxillofacial Surgery, vol. 43, (1985), 605-611.

Matuska, et al., "Autologous Solution Protects Bovine Cartilage Explants from IL-1a and STFa-Induced Cartilage Degradation", Journal of Orthopaedic Research, (Jul. 16, 2013), 7 pgs.

Mehmet, C, et al., "Autologous Fibrin Glue From Intraoperatively Collected Platelet-Rich Plasma", Ann Thorac Surg, vol. 53, (1992), 530-531.

Mehta, Sanjay, et al., "Gentamicin distribution from a collagen carrier", Journal of Orthopaedic Research, vol. 14, No. 5—Abstract, (Sep. 1, 1996), 749-754.

Molnar, Amy, "Stem Cells from Muscles Can Repair Cartilage, Study Finds Genetically Engineered Muscle-Derived Stem Cells Improved Cartilage Repair in Rats", American College of Rheumatology, (2005), 2 pgs.

Moretz, W., et al., "A simple autologous fibrinogen glue for otologic surgery", Otolarvnaol Head Neck Surg 95, (Jul. 1986), 122-4.

Nakagami, Hironori, et al., "Novel Autologous Cell Therapy in Ischemic Limb Disease Through Growth Factor Secretion by Cultured Adipose Tissue-Derived Stromal Cells", Angiogenesis by Adipose Tissue-Derived Cells, American Heart Association, Inc., (Dec. 2005), 2542-2547.

Nathan, Suresh, et al., "Cell-Based Therapy in the Repair of Osteochondral Defects: A Novel Use for Adipose Tissue", Tissue Engineering, vol. 9, No. 4, Mary Ann Liebert, Inc., (2003), 733-744.

Nilsson, et al., "Bone Repair Induced by Bone Morphogenetic Protein in Ulnar Defects in Dogs", The Journal of Bone and Joint Surgery, vol. 68 B., No. 4, (Aug. 1986), 635-642.

Okamoto, Y. et al., "Determination of soluble tumor necrosis factor-alpha receptor type (TNFRI) and II (TNFRII) in the urine of healthy Japanese subjects", Journal of Immunoassay and Immunochemistry, 2011, vol. 32,, (2011), 145-155.

Okunishi, K, et al., "Hepatocyte Growth Factor Significantly Suppresses Collagen-Induced Arthritis in Mice", The Journal of Immunology, vol. 179, No. 8, (Oct. 15, 2007), 15 pgs.

Orphardt, Charles E, "Denaturation of Proteins", Virtual Chembook, Elmhurst College, <http://www.elmhurst.edu/chm/vchembook/568denaturation.html> (web accessed Mar. 9, 2011), (2003), 3 pgs.

O'Shaughnessey, Krista, et al., "Autologous Protein Solution Prepared From the Blood of Osteoarthritic Patients Contains an Enhanced Profile of Anti-Inflammatory Cytokines and Anabolic Growth Factors", Journal of Orthopaedic Research, (Jun. 1, 2014), 1349-1355 pgs.

Parchment, et al., "Roles for in vitro myelotoxicity tests in preclincial drug development and clinical trial planning, Toxicology Pathology, Society of Toxicological Pathologists", vol. 21, No. 2, (1993), 241-250.

Parker, Anna M, et al., "Adipose-derived stem cells for the regeneration of damaged tissues", Expert Opinion, Cell- & Tissue-based Therapy, Expert Opin. Bioi. Ther., Informa UK Ltd, (2006), 567-578.

Planat-Benard, V., et al., "Spontaneous Cardiomyocyte Differentiation From Adipose Tissue Stroma Cells", Adipose-Derived Cell Cardiomyocyte, American Heart Association, Inc., (Feb. 6, 2004), 223-229.

Pommer, et al., "Dielectrophoretic separation of platelets from whole blood in microfluidic channels", Electrophoresis, (2008), 1213-1218.

Ponticiello, Michael S, "A Rapid Technique for the Isolation and Concentration of Stem Cells from Human Bone Marrow", Cell Factor Technologies, Inc., (2006), 1 pg.

Rader, C, et al., "Cytokine Response of Human Macrophage-like Cells After Contact With Polyethylene and Pure Titanium Particles", The Journal of Arthroplasty, vol. 14, No. 7, (Oct. 1999), 840-848.

Rangappa, Sunil, et al., "Transformation of Adult Mesenchymal Stem Cells Isolated From the Fatty Tissue Into Cardiomyocytes", Adult Stem Cells Transformed into Cardiomyoctyes, Ann Thorac Surg, (2003), 775-779.

Rigotti, M D., et al., "Clinical Treatment of Radiotherapy Tissue Damage by Lipoaspirate Transplant: A Healing Process Mediated by Adipose-Derived Adult Stem Cells", Plastic and Reconstructive Surgery, Breast, PRS Journal vol. 119, No. 5, Stem Cell Therapy for Angiogenesis, (Apr. 15, 2007), 1409-1422.

Robert, Quigley L, et al., "Intraoperative Procurement of Autologous Fibrin Glue", Ann Thorac Surg, vol. 56, (1993), 387-389.

Rubin, M. D., et al., "Clinical Treatment of Radiotherapy Tissue Damage by Lipoaspirate Transplant: A Healing Process Mediated by Adipose-Derived Adult Stem Cells", Plastic and Reconstructive Surgery, Discussion vol. 119, No. 5, Stem Cell Therapy for Angiogenesis, (Apr. 15, 2007), 1423-1424.

Sadeghi, M, et al., "Strikingly higher interleukin (IL)-1a, IL-1b and soluble interleukin-1 receptor antagonist (sIL-1RA) but similar IL-2, sIL-2R, IL-3, IL-4, IL-6, sIL-6R, IL-10, tumour necrosis factor (TNF)-a, transforming growth factor (TGF)-B2, (cont.)", (Title cont. "transforming growth factor (TGF)-(32 and interferon IFN-y urine Levels in healthy females compared to healthy males: protection against urinary tract injury?") Clinical and Experimental Immunology, vol. 142, (2005), 312-317.

Sanal, M, et al., "Does fibrin glue cause foreign body reactions?", Eu r J Pediatr Sura 2, (1992), 285-6.

(56) References Cited

OTHER PUBLICATIONS

Schaffler, Andreas, et al., "Concise Review: Adipose Tissue-Derived Stromal Cells—Basic and Clinical Implications for Novel Cell-Based Therapies", Tissue-Specific Stem Cells, Stem Cells®, (Apr. 10, 2007), 12 pgs.
Schmidt, K G, "Labelling of Human and Rabbit Platelets with Indium-Oxine Complex", (1979), 97-106.
Schmidt, K G, et al., "Preparation of Platelet Suspensions from Whole Blood in Buffer", Scand. J, Hoemato, 23, (1979), 88-96.
Semple, Elisabeth, et al., "Quality of Thrombin Produced From the Patient's Own Plasma Using the TPD™, a New Thrombin-Processing Device", Journal of American Society of Extra-Corporeal Technology, 37(2), (2005), 196-200.
Sevenoaks, Martin J., et al., "Chronic Obstructive Pulmonary Disease, inflammation and co-morbidity—a common inflammatory phenotype?", respiratory Research vol. 7:70, (2006), 1-9.
Shiozawa, Kazuko, et al., "Gene Therapy, Is a total therapy for rheumatoid arthritis possible?", Pharma Medica, vol. 17, No. 10 w/ partial English Translation, (1999), 16 pgs.
Shu-Li, Lin, et al., "Static magnetic field attenuates mortality rate of mice by increasing the production of IL-1 receptor antagonist", Int. J. Radiat. Biol. 2009, 85(7), (Jul. 31, 2009), 633-640.
Siedentop, Karl H, et al., "Autologous Fibrin Tissue Adhesive", Laryngoscope, vol. 95, (Sep. 1985), 1074-1076.
Siedentop, Karl H. et al., "Extended Experimental and Preliminary Surgical Findings with Autologous Fibrin Tissue Adhesive Made from Patient's Own Blood", Laryngoscope, vol. 96, (Oct. 1986), 1062-1064.
Sierra, D H, "Fibrin sealant adhesive systems: a review of their chemistry, material properties and clinical applications", J Biomater Appl 7, (Apr. 1993), 309-52.
Silver, Frederick H, et al., "Review Preparation and use of fibrin glue in surgery", Biomaterials 16 (1995), (1995), 891-903.
Solchaga, Luis A., et al., "Hyaluronic Acid-Based Polymers as Cell Carriers for Tissue-Engineered Repair of Bone and Cartilage", Journal of Orthopaedic Research, Orthopaedic Research Society, US, vol. 17, (Jan. 1, 1999), 205-213.
Solem, Jan Otto, et al., "Hemoconcentration by Ultrafiltration During Open-Heart Surgery", Scand J Thor Cardiovasc Surg 22, (1988), 271-274.
Spotnitz, William D, et al., "Successful Use of Fibrin Glue During 2 Years of Surgery at a University Medical Center", The American Surgeon, vol. 55,, (Mar. 1989), 166-168.
Sutton, Robin G, et al., "Comparison of Three Blood-Processing Techniques During and After Cardiopulmonary Bypass", Ann Thorac Surg (1993) vol. 56, (1993), 6 pgs.
Takahashi, Kazutoshi, et al., "Induction of Pluripotent Stem Cells from Adult Human Fibroblasts by Defined Factors", Cell, Elsevier Inc., (Nov. 30, 2007), 1-12.
Tawes, Jr., Roy L. et al., "Autologous Fibrin Glue: The Last Step in Operative Hemostatis", The American Journal of Surgery, vol. 168, (Aug. 1994), 120-122.
Thompson, et al., "Fibrin Glue: A Review of Its Preparation, Efficacy, and Adverse Effects as a Topical Hemostat", Drug Intelligence and Clinical Pharmacy, vol. 22, (Dec. 1988), 946-952.
Toriumi, Dean M, et al., "Surgical Tissue Adhesives in Otolaryngology—Head and Neck Surgery", Otolaryngologic Clinics of North America, vol. 27, No. 1, (Feb. 1994), 203-209.
Wang, "Cell separation by dielectrophoretic field-flow-fractionation", Analytical Chemistry, (2000), 832-839.
Weis-Fogh, U S, "Fibrinogen prepared from small blood samples for autologous use in a tissue adhesive system", Eur Surg Res 20, (1988), 381-9.
Weisman, M D, "Biochemical Characterization of Autologous Fibrinogen Adhesive", Laryngoscope 97, (Oct. 1987), 1186-1190.
Wiseman, David M, et al., "Wound Dressings: Design and Use", In Wound Healing: Biochemical & Clinical Aspects 1st ed., vol., (1992), 562-580.
Yoon, Eulsik, et al., "In Vivo Osteogenic Potential of Human Adipose-Derived Stem Cells/Poly Lactide-Co-Glycolic Acid Constructs for Bone Regneration in a Rat Critical-Sized Calvarial Defect Model", Tissue Engineering, vol. 13, No. 3, (2007), 619-627.
Zhang, Duan-Zhen, et al., "Transplantation of autologous adipose-derived stem cells ameliorates cardiac function in rabbits with myocardial infarction", Chinese Medical Journal, vol. 120, No. 4 General Hospital of Shenyang Military Region, (2007), 300-307.
Zuk, P. A, et al., "Multilineage cells from human adipose tissue: Implications for cellbased therapies", Tissue Engineering, 7(2), XP002198710, ISSN: 1076-3279, (Apr. 1, 2001), 211-228.
"U.S. Appl. No. 12/394,723, Non Final Office Action mailed Oct. 5, 2016", 16 pgs.
"U.S. Appl. No. 12/549,116, Non Final Office Action mailed Oct. 6, 2016", 15 pgs.
"U.S. Appl. No. 13/837,005, Advisory Action mailed Dec. 2, 2016", 3 pgs.
"U.S. Appl. No. 13/837,005, Response filed Oct. 24, 2016 to Final Office Action mailed Aug. 23, 2016", 9 pgs.
"U.S. Appl. No. 13/837,005, Response filed Dec. 22, 2016 to Advisory Action mailed Dec. 2, 2016", 10 pgs.
"U.S. Appl. No. 13/837,480, Non Final Office Action mailed Sep. 13, 2016", 9 pgs.
"U.S. Appl. No. 13/837,480, Response filed Dec. 12, 2016 to Non Final Office Action mailed Sep. 13, 2016", 13 pgs.
"U.S. Appl. No. 13/841,083, Final Office Action mailed Sep. 9, 2016", 10 pgs.
"U.S. Appl. No. 13/841,083, Response filed Nov. 29, 2016 to Final Office Action mailed Sep. 9, 2016", 12 pgs.
"U.S. Appl. No. 13/841,103, Final Office Action mailed Dec. 14, 2016", 24 pgs.
"U.S. Appl. No. 14/050,950, Notice of Allowance mailed Oct. 6, 2016", 12 pgs.
"U.S. Appl. No. 14/803,414, Response filed Dec. 19, 2016 to Restriction Requirement mailed Oct. 20, 2016", 7 pgs.
"U.S. Appl. No. 14/803,414, Restriction Requirement mailed Oct. 20, 2016", 7 pgs.
"U.S. Appl. No. 14/808,828, Non Final Office Action mailed Dec. 8, 2016", 10 pgs.
"U.S. Appl. No. 14/808,828, Response filed Oct. 3, 2016 to Restriction Requirement mailed Aug. 2, 2016", 7 pgs.
"U.S. Appl. No. 14/830,977, Final Office Action mailed Oct. 20, 2016", 12 pgs.
"U.S. Appl. No. 14/841,086, Examiners Interview Summary mailed Nov. 7, 2016", 3 pgs.
"Arthritis", Mayo Clinic, (Jan. 22, 2013), 1-5.
"Canadian Application Serial No. 2,772,069, Office Action mailed Jul. 20, 2016", 5 pgs.
"Chinese Application Serial No. 2011800457327, Office Action mailed Mar. 26, 2015", W/ Machine Translation, 18 pgs.
"Chinese Application Serial No. 2011800457327, Office Action mailed Jul. 16, 2014", W/ Machine Translation, 16 pgs.
"Chinese Application Serial No. 2011800457327, Response filed Jun. 10, 2015 to Office Action mailed Mar. 26, 2015", W/ English Claims, 22 pgs.
"Chinese Application Serial No. 2011800457327, Response filed Dec. 1, 2014 to Office Action mailed Jul. 16, 2014", W/ English Claims, 19 pgs.
"Chinese Application Serial No. 201480027178.3, Voluntary Amendment filed Jul. 15, 2016", w/English claims, 35 pgs.
"Chinese Application Serial No. 201480027408.6, Voluntary Amendment mailed Jun. 8, 2016", W/ English Claims, 50 pgs.
"European Application Serial No. 10749582.2, Communication Pursuant to Article 94(3) EPC mailed May 10, 2016", 4 pgs.
"European Application Serial No. 10749582.2, Communication Pursuant to Article 94(3) EPC mailed Sep. 10, 2013", 5 pgs.
"European Application Serial No. 10749582.2, Response filed Jan. 3, 2014 to Communication Pursuant to Article 94(3) EPC mailed Sep. 10, 2013", 12 pgs.
"European Application Serial No. 10749582.2, Response filed Apr. 16, 2015 to Communication Pursuant to Article 94(3) EPC mailed Dec. 8, 2014", 14 pgs.
"European Application Serial No. 10749582.2, Response filed Aug. 26, 2016 to Communication Pursuant to Article 94(3) EPC mailed May 10, 2016", 13 pgs.

(56) References Cited

OTHER PUBLICATIONS

"European Application Serial No. 10749582.2, Response filed Sep. 28, 2012 to Communication pursuant to Rules 161(2) and 162 EPC mailed Apr. 3, 2012", 19 pgs.

"European Application Serial No. 11754786.9, Communication Pursuant to Article 94(3) EPC mailed Feb. 19, 2014", 4 pgs.

"European Application Serial No. 11754786.9, Grounds for the decision mailed Oct. 13, 2015", 7 pgs.

"European Application Serial No. 11754786.9, Response filed Feb. 6, 2015 to Communication Pursuant to Article 94(3) EPC mailed Oct. 8, 2014", 9 pgs.

"European Application Serial No. 11754786.9, Response filed Aug. 13, 2014 to Communication Pursuant to Article 94(3) EPC mailed Feb. 19, 2014", 10 pgs.

"European Application Serial No. 11754786.9, Response filed Nov. 4, 2013 to Communication pursuant to Rules 161(1) and 162 EPC mailed Apr. 24, 2013", 21 pgs.

"European Application Serial No. 11754786.9, Summons to Attend Oral Proceedings mailed Mar. 10, 2015", 3 pgs.

"European Application Serial No. 14707069.2, Communication Pursuant to Article 94(3) EPC mailed Nov. 15, 2016", 7 pgs.

"European Application Serial No. 14707909.9, Response filed Dec. 6, 2016 to Communication Pursuant to Article 94(3) EPC mailed Jul. 22, 2016", 11 pgs.

"European Application Serial No. 14709014.6, Communication Pursuant to Article 94(3) EPC mailed Oct. 20, 2016", 12 pgs.

"European Application Serial No. 14709014.6, Response filed May 27, 2016 to Office Action mailed Nov. 19, 2015", 15 pgs.

"European Application Serial No. 15184504.7, Communication Pursuant to Article 94(3) EPC mailed Sep. 16, 2016", 5 pgs.

"Japanese Application Serial No. 2013-527119, Examiners Decision of Final Refusal mailed Oct. 18, 2016", W/ English Translation, 9 pgs.

Belal, Mahmoud Helmy, "Recombinant Human Platelet-Derived Growth Factor-BB: a promising role for fibroblast cell attachment in chronic periodontitis. A concentration-dependent effect on human cell adhesion: SEM study", Rev. Clin. Pesq. Odontol., Curitiba, v. 5, n. 3, (2009), p. 225-240.

Honore, Prisca, et al., "Interleukin-1aB gene-deficient mice show reduced nociceptive sensitivity in models of inflammatory and neuropathic pain but not post-operative pain", Behavioral Brain Research, (2006), 355-364.

Nalamachu, Srinivas, "An Overview of Pain Management: The Clinical Efficacy and Value of Treatment", Am. J. Manag. Care. 19, (2013), 261-266.

Sarzi-Puttini, Piercarlo, et al., "The Appropriate Treatment of Chronic Pain", Clin. Drug Investig. 32, (2012), 21-33.

Shrivastava, Abha, et al., "Effects of Electromagnetic Forces of Earth on Human Biological System", Indian J. Prev. Soc. Med, Retrieved from the Internet: <URL:http://medind.nic.in/ibl/t09/i3/iblt09i3p162.pdf>, (Jan. 1, 2009), 162-167.

Tiaka, Elisavet K., et al., "Epidermal Growth Factor in the Treatment of Diabetic Foot Ulcers: An Update", Perspectives in Vascular Surgery and Endovascular Therapy 24(1), (2012), p. 37-44.

Younger, Jarred, et al., "Pain Outcomes: A Brief Review of Instruments and Techniques", Curr Pain Headache Rep. 13(1), (Feb. 2009), p. 39-43.

\* cited by examiner

IMPLANTABLE DEVICE FOR PRODUCTION OF INTERLEUKIN-1 RECEPTOR ANTAGONIST

CROSS-REFERENCE TO RELATED APPLICATIONS

This application is a 371 U.S. National Stage of International Application No. PCT/US2010/046994, filed Aug. 27, 2010. This application claims the benefit of U.S. Provisional Application No. 61/237,484, filed Aug. 27, 2009. The disclosures of the above applications are incorporated herein by reference.

INTRODUCTION

The present technology relates to implantable devices that produce interleukin-1 receptor antagonist, and implantable devices and methods of using implantable devices for producing interleukin-1 receptor antagonist in vivo.

Interleukin-1 (IL-1) includes a family of cytokines that can stimulate lymphocytes and macrophages, activate phagocytes, increase prostaglandin production, contribute to degeneration of bone joints, increase bone marrow cell proliferation, and are involved in many chronic inflammatory conditions. IL-1 can be generated by macrophages, monocytes, and dendritic cells, and can be part of the inflammatory response against infection.

The mode of action of IL-1 can be mediated by interleukin-1 receptor antagonist protein (IL-1ra; also known as "IRAP"). IL-1ra binds to the same receptor on the cell surface as IL-1, and thus prevents IL-1 from sending a signal to that cell. IL-1ra is secreted from white blood cells, including monocytes, macrophages, neutrophils, polymorphonuclear cells (PMNs), and other cells, and can modulate a variety of IL-1 related immune and inflammatory responses, as described by Arend W P, Malyak M, Guthridge C J, Gabay C (1998) "Interleukin-1 receptor antagonist: role in biology" Annu. Rev. Immunol. 16: 27-55. Production of IL-1ra is stimulated by several substances including adherent immunoglobulin G (IgG), other cytokines, and bacterial or viral components. IL-1ra is an important natural anti-inflammatory protein in arthritis, colitis, and granulomatous pulmonary disease.

IL-1ra can be used in the treatment of rheumatoid arthritis, an autoimmune disease in which IL-1 plays a key role, reducing inflammation and cartilage degradation associated with the disease. For example, Kineret™ (anakinra) is a recombinant, non-glycosylated form of IL-1ra (Amgen Manufacturing, Ltd., Thousand Oaks, Calif.). Various recombinant interleukin-1 inhibitors and methods of treatment are described in U.S. Pat. No. 6,599,873, Sommer et al., issued Jul. 29, 2003; U.S. Pat. No. 5,075,222, Hannum et al., issued Dec. 24, 1991; and U.S. Application Publication No. 2005/0197293, Mellis et al., published Sep. 8, 2005 In addition, methods for producing IL-1ra from body fluids, including the use of autologous fluids, are described in U.S. Pat. No. 6,623,472, Reincke et al., issued Sep. 23, 2003; U.S. Pat. No. 6,713,246, Reinecke et al., issued Mar. 30, 2004; and U.S. Pat. No. 6,759,188, Reinecke et al., issued Jul. 6, 2004.

Compositions and methods using IL-1ra are known in the art. For example, IL-1ra has been delivered as part of a composition with hyaluronic acid, as described in U.S. Pat. No. 6,096,728, Collins et al., issued Aug. 1, 2000. However, many such methods and compositions are associated with issues regarding stability and half-life of IL-1ra as well as the amount and rate of IL-1ra provided. Accordingly, improved methods of producing and delivering IL-1ra are desirable and would be useful in treating conditions and pathologies mediated by the interleukin-1 receptor, including the management of inflammation.

SUMMARY

The present technology provides implantable devices and treatment methods using such devices to produce interleukin-1 receptor antagonist for managing one or more sites of inflammation in a human or animal subject. The implantable device produces interleukin-1 receptor antagonist when loaded with white blood cells or adipocytes. The implantable device includes an enclosed or substantially enclosed body defining an internal space where at least a portion of the body comprises a first bioresorbable material. A second bioresorbable material is within the internal space and the second bioresorbable material includes an activation surface. One or more voids are also within the internal space. The white blood cells are part of whole blood, platelet-rich plasma, or are isolated white blood cells. The adipocytes are part of adipose tissue or are isolated adipocytes. The treatment site, such as a site of inflammation, can be associated with arthritis, e.g., osteoarthritis. The IL-1ra produced by the implantable device can be derived from adipose tissue and/or whole blood obtained from the patient receiving the implantable device, thereby providing autologous IL-1ra.

BRIEF DESCRIPTION OF THE DRAWINGS

The present technology will become more fully understood from the detailed description and the accompanying drawings, wherein.

Figure 1:
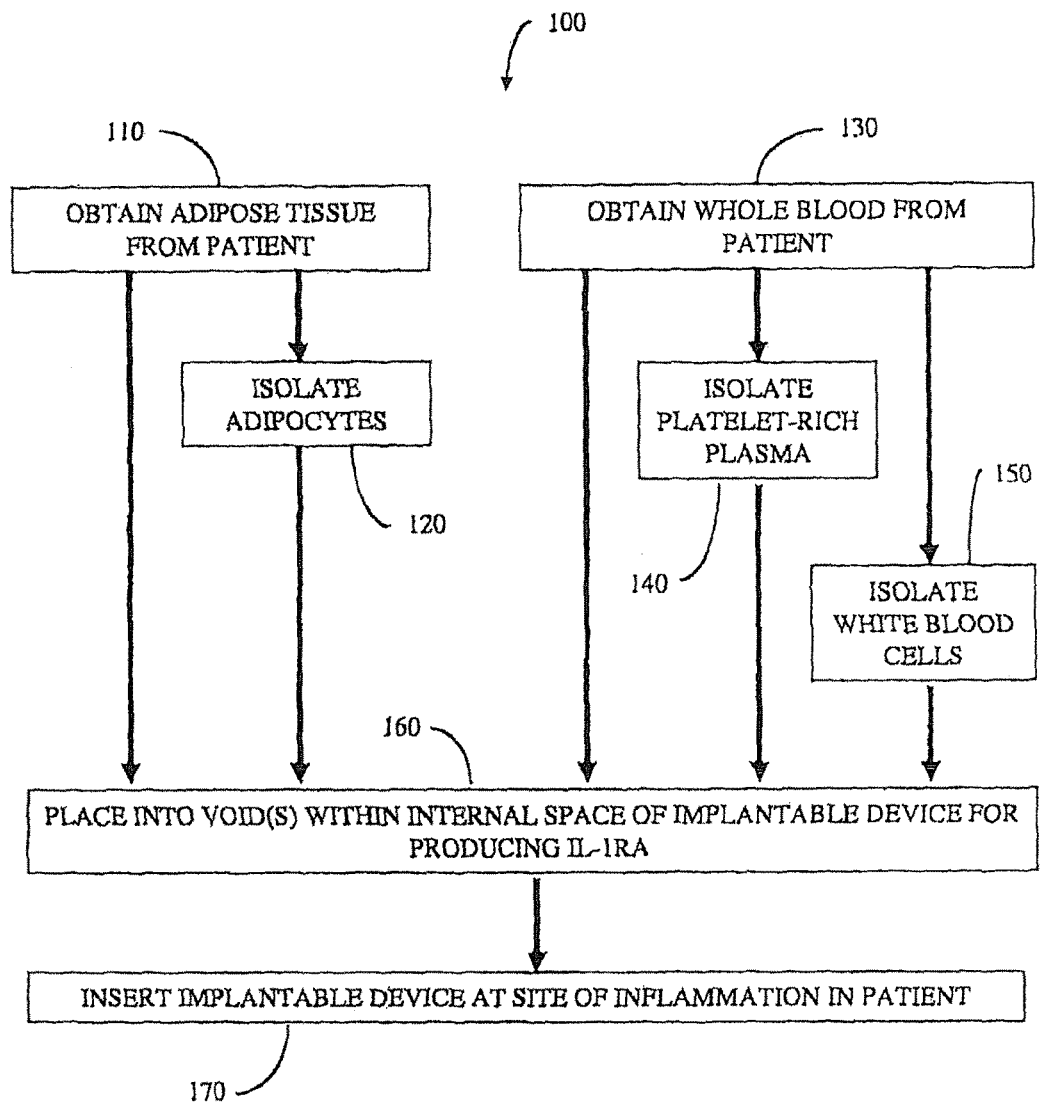
FIG. 1 is a diagrammatic illustration of a method to produce IL-1ra according to an embodiment of the present technology.

It should be noted that the figures set forth herein are intended to exemplify the general characteristics of materials and methods among those of the present technology, for the purpose of the description of certain embodiments. These figures may not precisely reflect the characteristics of any given embodiment, and are not necessarily intended to define or limit specific embodiments within the scope of this technology.

DETAILED DESCRIPTION

The description of the following technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Detailed Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The present technology relates to interleukin-1 receptor antagonist (IL-1ra), including methods of generating IL-1ra, compositions comprising IL-1ra produced by such methods, methods of using IL-1ra, treatment methods comprising IL-1ra, and devices for the generation, isolation, and administration of IL-1ra.

Implantable devices for producing interleukin-1 receptor antagonist when loaded with white blood cells or adipocytes can include the following aspects. In some embodiments, the implantable device comprises an enclosed or substantially enclosed body defining an internal space where at least a portion of the body includes a first bioresorbable material. Within the internal space of the body are a second bioresorbable material and one or more voids. The second bioresorbable material includes an activation surface to stimulate production of IL-1ra by cells placed within the device.

Without limiting the mechanism, utility, or function of the present technology, the activation surface of the second bioresorbable material appears to serve as an activator of IL-1ra production by adipocytes and white blood cells. In some respects, contact of the adipocytes and/or white blood cells with the activation surface of the second bioresorbable material appears to stimulate IL-1ra production and secretion by these cells. There also appears to be a correlation between the amount of IL-1ra produced and the concentration of white blood cells, where adipose tissue can include white blood cells. Thus, the present technology uses adipose tissue and disaggregated adipose tissue to obtain adipocytes, where white blood cells can be present in both the adipose tissue and the adipocytes obtained from adipose tissue. White blood cells can also be obtained from bone marrow.

The present implantable devices can further comprise the following aspects. One or more voids within the internal space may include white blood cells and/or adipocytes. For example, the white blood cells may be present in a medium selected from the group consisting of whole blood and/or platelet rich plasma. The adipocytes may be part of isolated adipose tissue; where, for example, the adipose tissue may include other cell types. Following loading and activation of the cells, the implantable device may produce from about 30,000 pg/mL to about 110,000 pg/mL of interleukin-1 receptor antagonist over an activation period of from about 30 seconds to about 24 hours.

Further aspects of the implantable devices include features relating to the enclosed or substantially enclosed body. For example, at least a portion of the body may comprise a self-healing material. Such self-healing materials include polysiloxane-organic hybrid copolymers, for example including components such as oligopeptides of alanine or glycine and polydimethylsiloxane (PDMS), which may further include side-grafted polypeptides or oligopeptides; self-healing polymers based on the bioresorbable materials described herein, such as poly-lactic acid; and hydrogels. The self-healing material allows use of a syringe, for example, to inject a volume of white blood cells and/or adipocytes into the one or more voids within the internal space. The body may also be substantially cylindrically shaped. For example, the enclosed or substantially enclosed body can be tubular with the internal space comprising the lumen. One end of the body may be open to expose the one or more voids within the internal space. In some cases, the one or more voids are operable to wick liquid into the one or more voids within the internal space and at least one of the one or more voids may be a longitudinal channel substantially traversing the length of the body. Such wicking by the void(s) may draw liquid and cells into the void via capillary action where the liquid and cells contact the activation surface of the second bioresorbable material within the internal space of the body.

The second bioresorbable material can include the following aspects. In some cases, the second bioresorbable material comprises a plurality of beads within the internal space of the body. The second bioresorbable material may be porous where the pores provide the activation surface. For example, the pores may be a few nanometers in average diameter and may be up to several hundred nanometers. In some cases, the activation surface of the second bioresorbable material may comprise immunoglobulin G. The second bioresorbable material may also comprise a texture, for example, where the surface has features ranging from the nanometer scale to features ranging from about 10 nanometers to several hundred nanometers in each of length, width, and height. The activation surface of the second bioresorbable material may comprise a surface to volume ratio of about 150,000 $m^{-1}$ to about 300,000 $m^{-1}$; e.g., spherical beads from about 20 microns to about 10 microns. The second bioresorbable material may also provide an activation surface comprising a surface area of about 50 $m^2/g$ to about 1,000 $m^2/g$ for the second bioresorbable material.

The first bioresorbable and second bioresorbable materials are biodegradable and are eroded or broken down by the patient's body following implantation. For example, the backbone of a bioresorbable polymer can be hydrolytically unstable; i.e., the polymer is unstable in a water based environment. As a result, bioresorption may occur in two stages. First, water penetrates the material, attacking the chemical bonds and converting long polymer chains into shorter water-soluble fragments. This can result in a reduction in molecular weight without the loss of physical properties, as the polymer can still be held together by the crystalline regions and/or crosslinking between chains, for example. Water can continue to penetrate the material over time and lead to metabolization of the fragments and bulk erosion. Second, surface erosion of the material occurs when the rate at which the water penetrating the device is slower than the rate of conversion of the polymer into water soluble materials. Degradation rate of the bioresorbable material may be therefore tailored according to the desired persistence of the implantable device, where choice of material and physical parameters, such as thickness, influence the rate of bioresorption.

Bioresorbable materials include synthetic polymers, natural polymers, polysaccharides, and combinations thereof. In some cases, the first and second bioresorbable materials comprise the same material and in other cases the first and second bioresorbable materials comprise different materials. Suitable synthetic polymers include polymers and copolymers of glycolic acid, L-lactic acid, D-lactic acid, urethane urea, trimethylene carbonate, dioxanone, $\epsilon$-caprolactone, hydroxybutyrate, orthoesters, orthocarbonates, aminocarbonates, anhydrides of at least one of sebacid acid, p-(carboxyphenoxy)propane, and p-(carboxyphenoxy)hexane, trimethylene carbonate, and combinations thereof. Suitable natural polymers include elastin, silk, fibrin, fibrinogen, collagen, gelatin, and combinations thereof. And suitable polysaccharides include hyaluronic acid, chitin, chitosan, alginate, carboxymethylcellulose, and combinations thereof. Other bioresorbable materials include those known in the biomedical arts including, for example, those used for bioresorbable sutures, dental devices, orthopedic fixation devices, tissue engineering scaffolds, and biodegradable vascular stents.

In some embodiments, the second bioresorbable material comprises a dry or dessicated material that is operable to absorb liquid. For example, the second bioresorbable material may be dehydrated gelatin beads that draw liquid from a volume of adipose tissue, adipocytes, whole blood, PRP, and/or white blood cells that are loaded into one or more voids of the implantable device. In this way, bulk solution or liquid, such as water, buffers, or blood, is drawn into the dry second bioresorbable material, thereby increasing the concentration and density of tissue and/or cells which are not absorbed into the dry material. The increased concentration and density can consequently provide for more contact between the tissue and/or cells and the activation surface of the second bioresorbable material.

The bioresorbable materials of the implantable device may also be porous or permeable so that IL-1ra produced therein may diffuse out of the body through the first bioresorbable material, for example. What is more, the permeability may allow other signaling molecules to diffuse out of the body as well as allowing such molecules to diffuse into the device from the surrounding implantation site. In some cases, the body may be sufficiently porous to allow cells to migrate into or out of the implantable device. As the first bioresorbable material degrades, for example, pores may form and/or existing pores may increase in size such that the rate of diffusion and/or cell migration increases over time. Eventually the second bioresorbable material within the internal space of the body begins to degrade and erode. At some point thereafter, the entire implantable device may be resorbed.

Referring now to FIG. 1, a flowchart 100 diagrammatically illustrates use of the present implantable device and production of IL-1ra for treating a site in a patient. Adipose tissue can be obtained from a patient as shown at step 110. This adipose tissue may be directly placed within the implantable device as per step 160, or may be processed to isolate adipocytes as shown in step 120. Whole blood can also be obtained from the patient as shown at step 130. The whole blood can be processed into platelet-rich plasma (PRP), as shown in step 140. For example, whole blood can be centrifuged to isolate PRP comprising white blood cells and platelets, which are located in the buffy coat layer following sedimentation. The whole blood can also be processed to isolate white blood cells, as per step 150.

At least one of the products of steps 110, 120, 130, 140, and 150 is then placed into one or more voids within the internal space of an implantable device, as per step 160. In some embodiments, two, three, four, or all five products are placed into the void(s); i.e., adipose tissue, adipocytes, whole blood, PRP, and/or white blood cells. In some embodiments, only adipose tissue is used and in other embodiments only PRP is used. One or more of these products may also be used in preparation of the other products. For example, whole blood may be used to resuspend cell pellets of isolated adipocytes and white blood cells. The adipose tissue in 110 and the whole blood in 130 may also be obtained from the patient receiving the implantable device in 170. In this way, the implantable device produces autologous IL-1ra.

As shown at step 160 of FIG. 1, once the implantable device is loaded with adipose tissue, adipocytes, whole blood, PRP, and/or white blood cells, the product(s) contact the activation surface of the second bioresorbable material. In some embodiments, contact can be for a time from about 30 seconds to about 72 hours and may be carried out at a temperature from about 20° C. to about 41° C. For example, the incubation may be from about one minute to about 48 hours, from about 5 minutes to about 12 hours, or from about 10 minutes to about 6 hours. In some embodiments, the implantable device may be incubated at about 37° C. during these time intervals. In other embodiments, the incubation may occur at ambient conditions, e.g., at a temperature of about 20-25° C. In some embodiments, the loaded implantable device is not incubated, but is instead inserted at the site of inflammation in the patient immediately after loading or within only a few minutes after loading.

Without limiting the mechanism, utility or function of the present technology, the activation surface of the second bioresorbable material serves as an activator of IL-1ra production by the adipose tissue, adipocytes, whole blood, PRP, and/or white blood cells. As described, the second bioresorbable material may also be a dry or dessicated material that absorbs liquid in addition to providing an activation surface to stimulate production of IL-1ra. In such cases, the second bioresorbable material not only activates production of IL-1ra, but also absorbs liquid from the volume of adipose tissue, adipocytes, whole blood, PRP, and/or white blood cells, thereby concentrating the tissue and/or cells relative to the activation surface.

Whole blood, platelet-rich plasma, and white blood cells may be obtained or isolated using methods known in the biomedical arts. For example, various devices may be used to generate platelet-rich plasma that includes a platelet concentration up to about 8-fold higher than whole blood and a white blood cell concentration up to about 5-fold higher than whole blood. The platelet rich plasma may comprise from about 80% to about 90% of the white blood cells present in the whole blood. Commercially available devices include the GPS® II Platelet Concentrate System, from Biomet Biologics, LLC (Warsaw, Ind., USA) and GPS® III Platelet Separation System, from Biomet Biologics, LLC (Warsaw, Ind., USA). Additional devices that may be used to isolate platelet-rich plasma at step 120 are also described, for example, in U.S. Pat. No. 6,398,972, Blasetti et al., issued Jun. 4, 2002; U.S. Pat. No. 6,649,072, Brandt et al., issued Nov. 18, 2003; U.S. Pat. No. 6,790,371, Dolocek, issued Sep. 14, 2004; U.S. Pat. No. 7,011,852, Sukavaneshvar et al., issued Mar. 14, 2006; U.S. Application Publication No. 2004/0251217, Leach et al., published Dec. 16, 2004 (incorporated by reference herein); U.S. Application Publication No. 2005/0109716, Leach et al., published May 26, 2005 (incorporated by reference herein); U.S. Application Publication No. 2005/0196874, Dorian et al., published Sep. 8, 2005 (incorporated by reference herein); and U.S. Application Publication No. 2006/0175242, Dorian et al., published Aug. 10, 2006 (incorporated by reference herein).

Other methods may be used to isolate platelet-rich plasma. For example, whole blood can be centrifuged without using a buoy system, whole blood may be centrifuged in multiple stages, continuous-flow centrifugation can be used, and filtration can also be used. In addition, a blood component including platelet-rich plasma can be produced by separating plasma from red blood cells using a slow speed centrifugation step to prevent pelleting of the platelets. In other embodiments, the buffy coat fraction formed from centrifuged blood can be separated from remaining plasma and resuspended to form platelet-rich plasma.

In addition to the GPS® Platelet Concentrate and Separation Systems, a variety of other commercially available devices may be used to isolate platelet-rich plasma at step 120, including the Magellan™ Autologous Platelet Separator System, commercially available from Medtronic, Inc. (Minneapolis, Minn., USA); SmartPReP™, commercially available from Harvest Technologies Corporation (Plymouth, Mass., USA); DePuy (Warsaw, Ind., USA); the Autolo-Gel™ Process, commercially available from Cytomedix, Inc. (Rockville, Md., USA); the GenesisCS System, commercially available from EmCyte Corporation (Fort Myers, Fla., USA); and the PCCS System, commercially available from Biomet 3i, Inc. (Palm Beach Gardens, Fla., USA).

Blood drawn from the patient may be mixed with an anticoagulant. Suitable anticoagulants include heparin, citrate phosphate dextrose (CPD), ethylenediaminetetraacetic acid (EDTA), anticoagulant citrate dextrose solution (ACD), and mixtures thereof. The anticoagulant may be placed in the syringe used for drawing blood from the subject, or may be mixed with the blood after it is drawn.

White blood cells may also be prepared using other methods known in the art. For example, white blood cells may be prepared from whole blood by lysing red blood cells or by centrifugation of whole blood utilizing a density gradient where the white blood cells sediment to the bottom of a centrifuge tube. An example of density centrifugation includes the Ficoll-Paque™ Plus (GE Healthcare Bio-Sciences, Piscataway, N.J., USA). In some cases, a density gradient may be used to further separate mononuclear and polymorphonuclear cells. White blood cells may also be prepared from whole blood using filtration; an example includes the Acelere™ MNC Harvest System (Pall Life Sciences, Ann Arbor, Mich., USA). White blood cells can also be obtained from bone marrow.

Adipose tissue refers to any fat tissue, either white or brown adipose tissue, which may be derived from subcutaneous, omental/visceral, mammary, gonadal, or other adipose tissue sites. In some embodiments, adipose tissue is derived from human subcutaneous fat isolated by suction assisted lipectomy or liposuction. Adipocytes may be isolated and/or freed from the adipose tissue and/or tissue portions using any suitable method, including methods known in the art such as mechanical and breakdown centrifugation. Adipocytes can also be isolated using enzymatic digestion. For example, adipocytes can be isolated from lipoaspirate, treated by sonication and/or enzymatic digestion, and enriched by centrifugation. Adipocytes isolated from adipose tissue may be washed and pelleted.

Methods for isolating adipose tissue and adipocytes can include the following aspects. Adipose tissue can be collected by suction-assisted tumescent liposuction inside a specialized collection container attached to suction hoses and to a liposuction cannula. The collection container can have a gauze-type grid filter that allows the tumescent fluid to pass through and retains the solid adipose tissue. After collecting the adipose tissue, the collection container is removed from the suction device and reattached to a centrifugation device. The filter unit may further contain a filter having approximately a 100 micrometer pore size. Once the collection container containing the adipose tissue is attached to the centrifugation device, the tissue is sonicated. After sonication, the entire apparatus is inserted into a centrifuge bucket and centrifuged at about 300×g for about 5 minutes. After centrifugation, the collection container together with the filter unit is detached and can be discarded. The pellet containing the adipocytes can be resuspended using one or more biocompatible solutions, such as autologous plasma, plasma concentrate, and platelet rich plasma.

Adipose tissue may also be treated with digestive enzymes and with chelating agents that weaken the connections between neighboring cells, making it possible to disperse the tissue into a suspension of individual cells, including adipocytes, without appreciable cell breakage. Following disaggregation, the adipocytes may be isolated from the suspension of cells and disaggregated tissue. For example, isolation of adipocytes may be performed by obtaining subcutaneous adipose tissue from lipoaspiration/liposuction procedures and digesting the tissue in collagenase type I solution (Worthington Biochemical Corp., Lakewood, N.J.) under gentle agitation for about 1 hour at 37° C. The dissociated cells may be filtered with 500 µm and 250 µm Nitex filters. The fraction is centrifuged at about 300×g for about 5 minutes. The supernatant is discarded and the cell pellet is resuspended in a compatible liquid solution, such as a blood-derived solution.

In some embodiments, adipocytes are prepared as follows. Adipose tissue is minced into small pieces (about 1 cm$^3$) and digested in 2 mg/mL type I collagenase (Worthington Biochemical Corp., Lakewood, N.J.) under intermittent mechanical agitation in a water bath at 37° C. for about 180 minutes. Digestion can be neutralized by the addition of medium or a blood-derived solution. The dissociated cells may be filtered with 500 μm and/or 250 μm Nitex filters. The cell suspension is centrifuged (300×g for 7 minutes at 25° C.) followed by removal of the supernatant from the cell pellet. The pellet is then resuspended in a compatible solution to provide a liquid volume comprising adipocytes.

Various methods and devices for isolating and/or fractionating adipose tissue include those as described by U.S. Pat. Nos. 7,374,678 and 7,179,391 to Leach et al. and U.S. Pub. Nos. 2009/0014391, 2008/0283474, and 2007/0208321 to Leach et al. A device, such as the GPS™ Platelet Concentrate System (Biomet, Warsaw, Ind.), may be used to isolate adipocytes. These methods may include obtaining adipocytes by performing lipoaspiration on the patient to obtain adipose tissue, enzymatically digesting the adipose tissue, and separating and/or washing the adipocytes using these devices.

Referring again to FIG. 1, once the implantable device is loaded in step 160, the activation surface of the second bioresorbable material activates the generation of IL-1ra by the adipose tissue, adipocytes, whole blood, PRP, and/or white blood cells. The implantable device is then inserted at a site of inflammation in a patient, as shown at step 170, such as a site of osteoarthritis.

The implantable device may be inserted in step 170 to provide IL-1ra at or near a site of inflammation in a human or animal subject (i.e., a patient). The patient receiving the IL-1ra-rich solution may be the same patient from whom the adipose tissue and/or whole blood are derived in steps 110 and 130. In this case, the method provides an autologous preparation of IL-1ra. Administration of the implantable device may be performed using various means, such as by injection of the implantable device using a syringe, cannulated device, surgical application, or application concomitant with another surgical procedure. It should be understood, however, that step 170 may comprise any biomedically acceptable process or procedure by which the implantable device is inserted, implanted, injected, or otherwise administered in or in proximity to a site in order to mediate effects related to stimulation of the interleukin-1 receptor, such as inflammation and inflammation due to osteoarthritis. For example, for treating inflammation caused by arthritis, an implantable device for producing autologous IL-1ra may be administered to the patient via a cannulated device. Implantation may be at or into the synovial space of an inflamed joint, or otherwise at or near the joint.

The present implantable devices may be sterilized by prior to loading with adipose tissue, adipocytes, whole blood, PRP, and/or white blood cells. For example, chemical sterilization or irradiation may be used to sterilize the implantable device and the device may be loaded using biomedically accepted sterile technique. In addition, an antibiotic may be included in the implantable device or added to one or more of the adipose tissue, whole blood, and products thereof loaded into the device; e.g., adipose tissue, adipocytes, whole blood, PRP, and/or white blood cells.

The present technology provides an implantable device capable of producing IL-1ra in vivo following implantation, including autologous IL-1ra, which reduces and/or substantially eliminates immunological issues that may arise when using non-autologous material or recombinant material. In addition, since the IL-1ra is produced by the patient's cells, natural post-translational modifications, such as glycosylation, are already present. This is not the case with most recombinant proteins since they are produced in prokaryotic hosts.

The implantable device can produce IL-1ra within minutes of loading with adipose tissue, adipocytes, whole blood, PRP, and/or white blood cells and can continue to produce to IL-1ra for up to 24 hours or more. For example, the implantable device can produce about 34,000 pg/mL to about 108,000 pg/mL of IL-1ra. It is understood, however, the concentrations present in any given solution may vary depending on the initial levels of components present in the adipose tissue, adipocytes, and/or source of white blood cells used in the present methods, and that increases in concentration are relative to those initial levels. In general, IL-1ra is produced at concentrations of at least about 10,000 pg/mL, at least about 25,000 pg/mL, or at least about 30,000 pg/mL, and can be up to 108,000 pg/mL or more. As the first bioresorbable material of the body of the implantable device begins to erode following implantation, the IL-1ra produced therein will contact the area at the implantation site at or near the site of inflammation. The first bioresorbable material may be porous and/or permeable to allow IL-1ra to begin diffusing out from the device even before the bioresorbable materials begin to degrade.

The implantable device for producing IL-1ra may be used to mediate effects of IL-1 and attenuate signaling via the interleukin-1 receptor. The IL-1ra produced from the implantable device may be used to block the biologic activity of naturally occurring IL-1, including inflammation and cartilage degradation associated with arthritis, by competitively inhibiting the binding of IL-1 to the interleukin-1 type receptor, which is expressed in many tissues and organs. For example, bone resorption and tissue damage such as cartilage degradation as a result of loss of proteoglycans due to IL-1 may be treated by administration of the IL-1ra-rich solution. In patients with arthritis, endogenous IL-1ra may not be present in effective concentrations in synovium and synovial fluid to counteract IL-1 concentrations in these patients, and hence the implantable device for producing IL-1ra may be inserted to treat these conditions and these sites. Size of the device, administration and implantation methods, and frequency of treatment may be modified based on established medical practices to achieve effective treatment. The present technology also includes methods of treating one or more sites of inflammation in a patient by using one or more implantable devices at an inflammation site or using one or more devices at multiple inflammation sites.

As one example, the implantable device for producing IL-1ra is inserted into a patient's knee joint using a cannulated device. The device produces IL-1ra in vivo that diffuses outward from the device to contact the immediate space around one or more of the patient's femur, tibia, fibula, patella, and cartilage. It should be understood, however, that the implantation site may be in any joint of a human or animal patient, including shoulders, elbows, wrists, ankles, hips, and the spinal column. In addition, the present methods and devices may be used to treat inflammation in sites within other tissues, such as muscle and tendon.

The present technology can include aspects of U.S. Provisional Application No. 61/031,803 filed Feb. 27, 2008, U.S. Provisional Application No. 61/116,940 filed Nov. 21, 2008, and U.S. Provisional Application No. 61/155,048 filed Feb. 24, 2009 and includes aspects of PCT/US2009/035541 filed Feb. 27, 2009.

The following specific examples are provided for illustrative purposes of how to make and use the compositions and methods of this technology and, unless explicitly stated otherwise, are not intended to be a representation that given embodiments of this technology have, or have not, been made or tested Example 1

Figure 2:
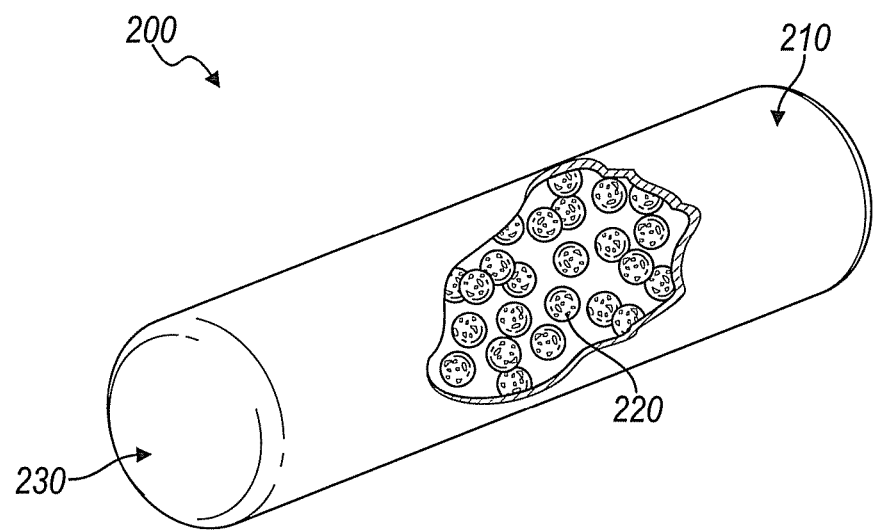
FIG. 2 is a perspective view with a cut-away of a first implantable device according to an embodiment of the present technology.

With reference to FIG. 2, an embodiment of an implantable device 200 is shown for producing interleukin-1 receptor antagonist in vivo when loaded with white blood cells or adipose tissue. The implantable device 200 includes an enclosed tubular body including a lumen where the tubular body comprises a first bioresorbable material 210. A second bioresorbable material 220 is within the lumen of the tubular body, as shown in the cut-out portion. The second bioresorbable material 220 comprises a plurality of gelatin beads from about 10 microns to about 20 microns in diameter. One end of the tubular body comprises a self-healing surface 230 that can be pierced with one or more needles for loading adipose tissue, adipocytes, whole blood, PRP, and/or white blood cells into the lumen of the device 200. The self-healing surface 230 is operable to substantially seal the puncture hole once loading is complete and the needle(s) is withdrawn. In this way, the beads of the second bioresorbable material 220 and the loaded adipose tissue, adipocytes, whole blood, PRP, and/or white blood cells do not leak out of the device 200.

Example 2

Figure 3:
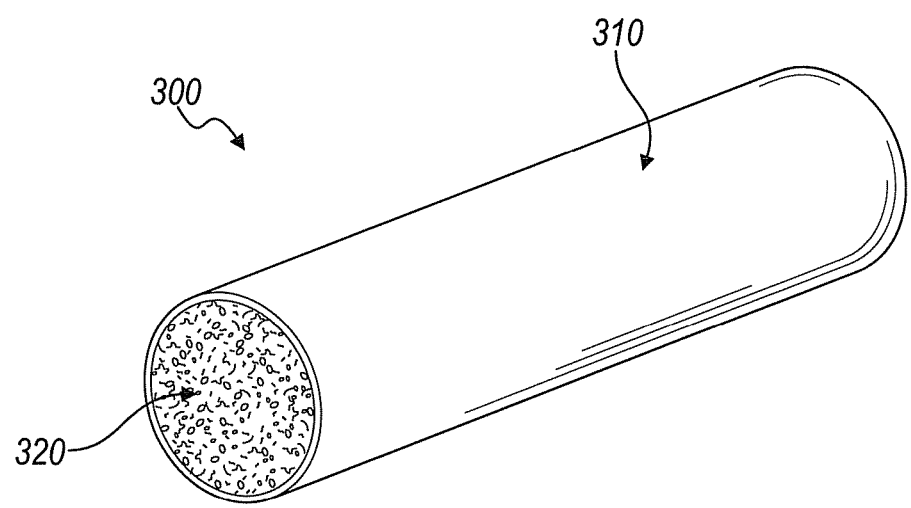
FIG. 3 is a perspective view of a second implantable device according to an embodiment of the present technology.

With reference to FIG. 3, an embodiment of an implantable device 300 is shown for producing interleukin-1 receptor antagonist in vivo when loaded with white blood cells or adipose tissue. The implantable device 300 has a tubular body comprising a first bioresorbable material 310. The tubular body includes a lumen and at least one open end exposing a porous second bioresorbable material 320 within the lumen. The porous second bioresorbable material is capable of activating adipose tissue, adipocytes, whole blood, platelet rich plasma, and/or white blood cells to produce IL-1ra. The lumen includes one or more voids intermixed with the porous second bioresorbable material 320 where the void(s) are operable to wick liquid into the lumen.

The open end of the implantable device 300 is contacted with a solution including adipose tissue, adipocytes, whole blood, platelet rich plasma, and/or white blood cells so that the solution is wicked into the void(s) within the lumen to load the device.

Example 3

Figure 4:
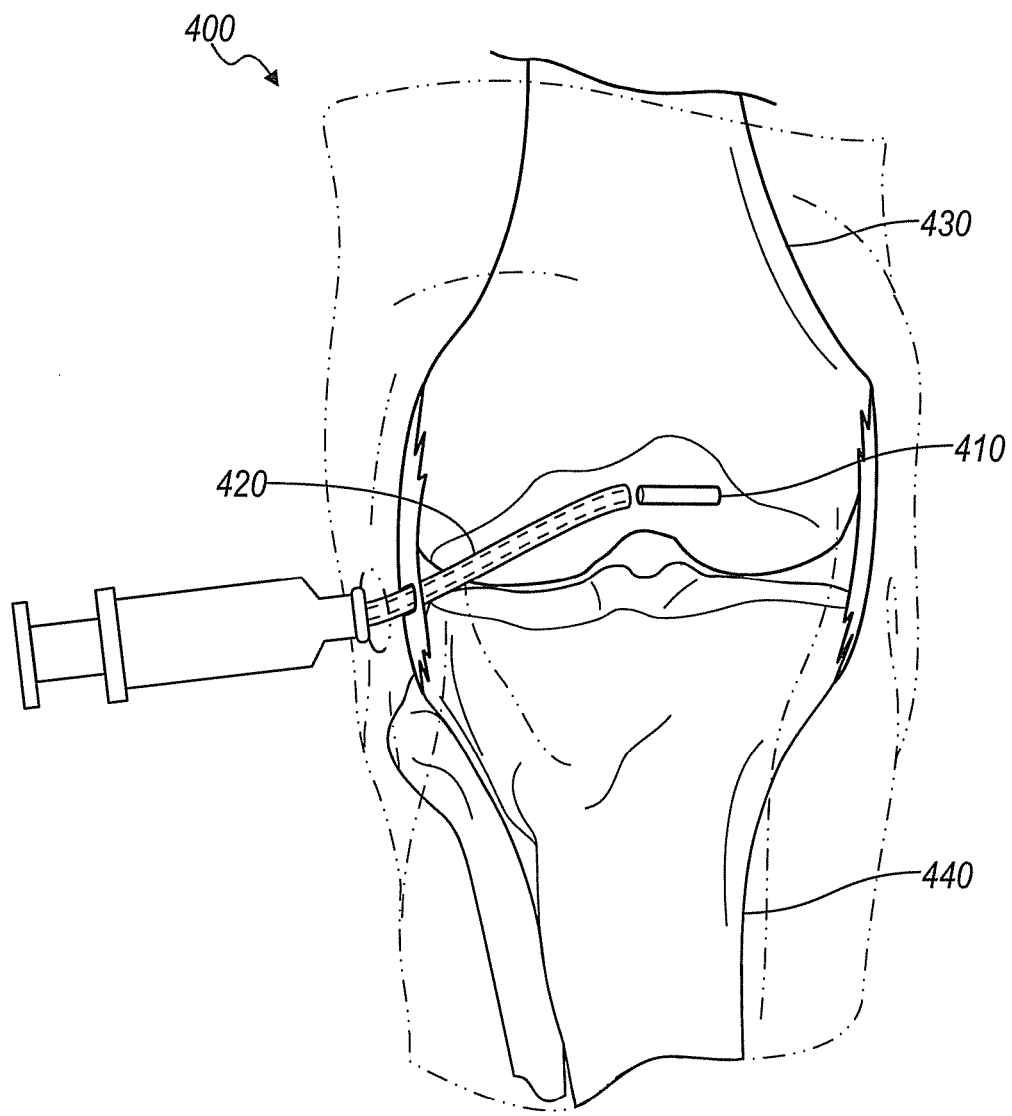
FIG. 4 is an illustration of administration of an implantable device to a knee joint according to an embodiment of the present technology.

With reference to FIG. 4, an embodiment of a treatment 400 using the present technology includes delivering an embodiment of the present implantable device 410 using a cannulated device 420. A movable element (not shown) is disposed within a portion of the cannulated device 420 and the implantable device 410 is originally disposed within a portion of the cannula device 420. The movable element is operable to expel the implantable device 410 from the cannulated device 420 into position at or near a site of inflammation, as shown. The implantable device 410 is loaded with white blood cells or adipocytes and produces interleukin-1 receptor antagonist in vivo at the implantation site. As shown in FIG. 4, the implantation site is proximate to the end of the patient's femur near the knee joint.

The examples and other embodiments described herein are exemplary and not intended to be limiting in describing the full scope of compositions and methods of this technology. Equivalent changes, modifications and variations of specific embodiments, materials, compositions and methods may be made within the scope of the present technology, with substantially similar results.

What is claimed is:

1. A method for treating a site of inflammation in a patient, the method comprising:
   providing an implantable device having an outer body comprising a first bioresorbable material and defining an internal space, the internal space having a second bioresorbable material, comprising gelatin, carboxymethylcellulose, or a combination thereof, and one or more voids disposed therein;
   injecting a liquid volume comprising adipose tissue, adipocytes, whole blood, platelet-rich plasma, white blood cells, or a combination thereof, into the one or more voids of the implantable device;
   implanting the implantable device at or proximate to the site of inflammation in the patient; and
   activating a plurality of cells in the liquid volume to generate interleukin-1 receptor antagonist (IL-1ra), including causing the liquid volume to contact the gelatin, carboxymethylcellulose, or a combination thereof, to activate the plurality of cells to generate IL-1ra.

2. A method for treating a site of inflammation in a patient, comprising:
   loading one or more voids of an implantable device with a liquid volume comprising adipose tissue, adipocytes, whole blood, platelet-rich plasma, white blood cells, or a combination thereof;
   inserting a cannulated device into the site of inflammation in the patient, including positioning the implantable device within a cannula of the cannulated device;
   moving a movable element of the cannulated device to expel the implantable device from the cannula, thereby implanting the implantable device at or proximate to the site of inflammation in the patient; and
   activating a plurality of cells within the liquid volume to generate interleukin-1 receptor antagonist (IL-1ra), wherein the implantable device comprises:
      an enclosed or substantially enclosed body defining an internal space, wherein at least a portion of the body comprises a first bioresorbable material;
      a second bioresorbable material within the internal space, the second bioresorbable material comprising gelatin, carboxymethylcellulose, or a combination thereof defining an activation surface to activate the plurality of cells to generate IL-1ra when the plurality of cells contact the activation surface; and
      one or more voids within the internal space.

3. A method for treating a site of inflammation in a patient, comprising:
   injecting into one or more voids of a lumen of an implantable device a liquid volume comprising adipose tissue, adipocytes, whole blood, platelet-rich plasma, white blood cells, or a combination thereof;
   activating a plurality of cells within the liquid volume to generate interleukin-1 receptor antagonist, including causing the plurality of cells to contact an activation surface of the implantable device; and implanting the implantable device at or proximate to the site of inflammation in the patient; wherein the implantable device comprises:

an enclosed tubular body including a lumen, the tubular body comprising a first bioresorbable material, wherein at least one end of the tubular body comprises a self-healing surface;

a porous second bioresorbable material within the lumen and exposed by piercing the self-healing surface, the second bioresorbable material comprising gelatin, carboxymethylcellulose, or a combination thereof to activate the plurality of cells to generate IL-1ra.

4. The method according to claim 1, wherein the white blood cells are present in whole blood, platelet-rich plasma, or a combination thereof.

5. The method according to claim 1, wherein the adipocytes are present in adipose tissue.

6. The method according to claim 1, wherein at least a portion of the body further comprises a self-healing material.

7. The method according to claim 1, wherein the activating occurs within 30 second of contact of the liquid volume with the second bioresorbable material.

8. The method according to claim 1, wherein the body comprises at least one end that is open to expose the one or more voids within the internal space.

9. The method according to claim 1, wherein the second bioresorbable material comprises a plurality of beads.

10. The method according to claim 1, wherein the second bioresorbable material is porous, wherein the pores provide the activation surface.

11. The method according to claim 1, wherein the second bioresorbable material further comprises immunoglobulin G.

12. The method according to claim 1, wherein the first and second bioresorbable materials independently comprise a synthetic polymer, a natural polymer, a polysaccharide, or a combination thereof.

13. The method according to claim 10, wherein the pores are from about 1 nanometer to about 10 nanometers in average diameter.

14. The method according to claim 1, wherein the activation surface of the second bioresorbable material comprises a surface to volume ratio of about 150,000 $m^{-1}$ to about 300,000 $m^{-1}$.

15. The method according to claim 1, wherein at least one of the one or more voids is a longitudinal channel traversing the entire length of the body.

16. The method according to claim 1, wherein injecting the liquid volume includes wicking the liquid volume into the one or more voids.

17. The method according to claim 1, wherein activating further includes allowing the second bioresorbable material to absorb a portion of the liquid volume.

18. The method according to claim 1, wherein the second bioresorbable material comprises a dry or a desiccated bioresorbable material configured to absorb at least a portion of the liquid volume.

19. The method according to claim 1, wherein activating further includes allowing the second bioresorbable material to absorb at least a portion of the liquid volume to cause the plurality of cells to become concentrated within the one or more voids so as to contact the activation surface.

20. A method for treating a site of inflammation in a subject, comprising:

providing or receiving an implantable device comprising a shell at least partially formed of a first bioresorbable material and defining a lumen, a second bioresorbable material comprising gelatin, carboxymethylcellulose, or a combination thereof, disposed within the lumen to activate adipocytes, white blood cells, or both to generate interluken-1 receptor antagonist (IL-1ra);

injecting a liquid volume into at least one void within the lumen, the liquid volume comprising a plurality of cells including adipocytes, white blood cells, or a combination thereof;

activating the plurality of cells to generate IL-1ra, including causing the plurality of cells to contact the gelatin, carboxymethylcellulose, or a combination thereof; and implanting the implantable device at or proximate to the site of inflammation in the subject.

21. The method of claim 20, wherein the step of implanting the implantable device in the subject occurs within 10 minutes or less after injecting the liquid volume.

22. The method of claim 20, wherein the step of activating occurs at temperature between 20° C. and 25° C.

23. The method of claim 20, wherein the at least one void comprises a plurality of voids, and wherein injecting includes allowing the liquid volume to wick through the plurality of voids.

24. The method of claim 20, wherein the second bioresorbable material comprises a plurality of pores, and wherein activating occurs within the plurality of pores.

25. The method of claim 20, wherein activating the plurality of cells further includes allowing the second bioresorbable material to absorb a portion of the liquid volume such that the density or the concentration of the plurality of cells is increased in the at least one void.

26. The method of claim 20, wherein allowing the liquid volume to wick from the at least one void into other ones of the plurality of voids includes causing a density or a concentration of the plurality of cells to increase in the plurality of voids.

27. The method of claim 20, wherein allowing the liquid volume to wick from the at least one void into other ones of the plurality of voids includes causing the liquid to be drawn toward or into the second bioresorbable material.

28. A method for treating a site of inflammation in a subject, the method comprising:

providing or receiving an implantable device comprising shell defining a lumen, the shell at least partially formed of a self-healing first bioresorbable material, a second bioresorbable material disposed within the lumen, the second bioresorbable material including gelatin, carboxymethylcellulose, or a combination thereof, to activate adipocytes, white blood cells, or a combination thereof to generate interluken-1 receptor antagonist;

injecting a liquid volume into at least one void formed by the lumen, the second bioresorbable material, or both, the liquid volume comprising a plurality of adipocytes, white blood cells, or a combination thereof, including piercing the self-healing first bioresorbable material;

activating the plurality of adipocytes, white blood cells, or the combination thereof to generate IL-1ra, including allowing the second bioresorbable material to absorb at least a portion of the liquid volume; and implanting the implantable device at or proximate to the site of inflammation in the subject.

29. The method of claim 28, further comprising healing the self-healing first bioresorbable material after piercing the self-healing first bioresorbable material.

30. The method of claim 29, wherein the self-healing first bioresorbable material comprises a polysiloxane-organic hybrid copolymer.

31. The method of claim 30, wherein the polysilioxane organic hybrid copolymer includes a polypeptide or an oligopeptide of alanine or glycine.

32. The method of claim 29, wherein the self-healing first bioresorbable material comprises a hydrogel.

33. The method of claim 28, wherein the at least one void includes a longitudinal channel traversing the entire length of the shell, the longitudinal channel in fluid communication with the second bioresorbable material.

34. The method of claim 28, wherein the activating occurs at a temperature between 20° C. and 25° C.

35. The method of claim 28, wherein the activating occurs within 10 minutes or less after injecting the liquid volume.

36. The method of claim 28, wherein activating further includes causing the density or the concentration of the plurality of cells to be increased in the lumen.

37. The method of claim 36, wherein the density or the concentration of the plurality of cells is increased by allowing the second bioresorbable material to absorb a liquid portion of the liquid volume.

\* \* \* \* \*

UNITED STATES PATENT AND TRADEMARK OFFICE
CERTIFICATE OF CORRECTION

PATENT NO. : 9,763,875 B2
APPLICATION NO. : 13/392266
DATED : September 19, 2017
INVENTOR(S) : Higgins et al.

Page 1 of 3

It is certified that error appears in the above-identified patent and that said Letters Patent is hereby corrected as shown below:

On the Title Page

On page 4, in Column 1, item (56), under "Other Publications", Line 12, delete "toher acive" and insert --other active-- therefor On page 4, in Column 1, item (56), under "Other Publications", Line 30, delete "II-1Ra" and insert --IL-1Ra-- therefor On page 4, in Column 1, item (56), under "Other Publications", Line 55, delete "IL-1beta" and insert --IL-1β-- therefor On page 4, in Column 1, item (56), under "Other Publications", Line 65, delete ""Therapuetic" and insert --"Therapeutic-- therefor On page 4, in Column 2, item (56), under "Other Publications", Line 1, delete ""Intratrachael" and insert --"Intratracheal-- therefor On page 4, in Column 2, item (56), under "Other Publications", Line 6, delete "IL-1beta and TNFalpha-stimulated" and insert --IL-1β and TNFα-stimulated-- therefor On page 6, in Column 1, item (56), under "Other Publications", Line 9, delete "Summary"," and insert --Summary Received Jan. 29, 2016",-- therefor On page 6, in Column 2, item (56), under "Other Publications", Line 71, delete "2010800428565,Response" and insert --2010800428565, Response-- therefor On page 7, in Column 1, item (56), under "Other Publications", Line 41, delete "09715775.4,Response" and insert --09715775.4, Response-- therefor Signed and Sealed this
Sixteenth Day of July, 2019

Andrei Iancu
*Director of the United States Patent and Trademark Office*

CERTIFICATE OF CORRECTION (continued)
U.S. Pat. No. 9,763,875 B2

On page 7, in Column 1, item (56), under "Other Publications", Line 43, delete "09715775.4,Supplemental" and insert --09715775.4, Supplemental-- therefor On page 8, in Column 1, item (56), under "Other Publications", Line 13, delete "Opinon" and insert --Opinion-- therefor On page 9, in Column 1, item (56), under "Other Publications", Line 60, delete "TGFb1" and insert --TGF$\beta_1$-- therefor On page 9, in Column 2, item (56), under "Other Publications", Line 3, delete "Factor-?1" and insert --Factor-$\beta_1$-- therefor On page 10, in Column 1, item (56), under "Other Publications", Line 64, delete "caltilage" and insert --cartilage-- therefor On page 10, in Column 2, item (56), under "Other Publications", Line 35, delete "ensor" and insert --tensor-- therefor On page 10, in Column 2, item (56), under "Other Publications", Line 45, delete "II-1 Ra" and insert --IL-1Ra-- therefor On page 10, in Column 2, item (56), under "Other Publications", Line 50, delete "homrone" and insert --hormone-- therefor On page 11, in Column 1, item (56), under "Other Publications", Line 50, delete "IL-1a and STFa-Induced" and insert --IL-1α and TNFα-Induced-- therefor On page 11, in Column 2, item (56), under "Other Publications", Line 8, delete "factor-alpha" and insert --factor-α-- therefor On page 11, in Column 2, item (56), under "Other Publications", Line 24, delete "preclincial" and insert --preclinical-- therefor On page 11, in Column 2, item (56), under "Other Publications", Line 62, delete "(IL)-1a, IL-1b" and insert --(IL)-1α, IL-1β-- therefor On page 11, in Column 2, item (56), under "Other Publications", Line 65, delete "(TNF)-a," and insert --(TNF)-α,-- therefor On page 11, in Column 2, item (56), under "Other Publications", Line 65, delete "(TGF)-B2," and insert --(TGF)-$\beta_2$,-- therefor On page 11, in Column 2, item (56), under "Other Publications", Line 66, delete "(TGF)-(32" and insert --(TGF)-$\beta_2$-- therefor

CERTIFICATE OF CORRECTION (continued)
U.S. Pat. No. 9,763,875 B2

On page 11, in Column 2, item (56), under "Other Publications", Line 67, delete "IFN-y" and insert --IFN-γ-- therefor On page 12, in Column 2, item (56), under "Other Publications", Line 1, delete "Regneration" and insert --Regeneration-- therefor On page 12, in Column 2, item (56), under "Other Publications", Line 8, delete "cellbased" and insert --cell-based-- therefor On page 13, in Column 2, item (56), under "Other Publications", Line 11, delete ""Interleukin-1aB" and insert --"Interleukin-1αβ-- therefor In the Claims In Column 14, Line 7, in Claim 20, delete "interluken-1" and insert --interleukin-1-- therefor In Column 14, Line 52, in Claim 28, delete "interluken-1" and insert --interleukin-1-- therefor In Column 15, Line 4, in Claim 31, delete "polysilioxane" and insert --polysiloxane-- therefor